United States Patent [19]

McKown

[11] Patent Number: 5,687,733

[45] Date of Patent: Nov. 18, 1997

[54] SYSTEM AND METHOD FOR ESTIMATING CARDIAC OUTPUT

[75] Inventor: Russell McKown, Richardson, Tex.

[73] Assignee: Baxter International Inc., Deerfield, Ill.

[21] Appl. No.: 548,937

[22] Filed: Oct. 26, 1995

[51] Int. Cl.⁶ ............................................. A61B 5/029
[52] U.S. Cl. .............................. 128/692; 128/713
[58] Field of Search ................................ 128/691, 692, 128/713, 736, 668

[56] References Cited

U.S. PATENT DOCUMENTS

| | | | |
|---|---|---|---|
| 4,238,527 | 12/1980 | Newbower et al. | 128/692 |
| 4,507,974 | 4/1985 | Yelderman | 128/713 |
| 5,146,414 | 9/1992 | McKown et al. | 128/713 |
| 5,357,967 | 10/1994 | Dixon et al. | 128/713 |
| 5,363,856 | 11/1994 | Hughes et al. | 128/713 |

OTHER PUBLICATIONS

Yelderman, M., *J. Clinical Monitoring* vol. 6 (Oct. 1990), pp. 322-332, "Continuous Measurement of Cardiac Output with the Use of Stochastic Identification Techniques".

*Primary Examiner*—Jennifer Bahr
*Assistant Examiner*—Eric F. Winakur
*Attorney, Agent, or Firm*—Jeffrey Slusher; Guy Cumberbatch; Bruce Canter

[57] ABSTRACT

Cardiac output CO is separately estimated in a local estimator and a trend estimator to provide CO values. A thermal signal is injected preferably according to a pseudo-random binary sequence signal profile at an upstream position in a blood flow region of a patient's body and is sensed as an indicator output signal at a downstream position. Low-frequency noise is preferably removed from the sensed indicator output signal. The local and trend estimations are based on measured frequency-domain transfer function values between the sensed and input indicator signal in relation to a pre-determined transfer function model, which is preferably a lagged normal model. The trend estimator is preferably a Kalman filter. The local estimator preferably forms its estimate based on non-recursive optimization of a cost function. The local estimator preferably provides initial values to start the trend estimator.

24 Claims, 9 Drawing Sheets

SYSTEM AND METHOD FOR ESTIMATING CARDIAC OUTPUT

BACKGROUND OF THE INVENTION

1. Field of the Invention

This invention relates to the in-vivo determination and display of estimates of the cardiac output of a patient.

2. Description of the Related Art

Information about the output of a patient's heart is very valuable to a surgical team, or to physicians who are trying to diagnose an illness or monitor the patient's condition. Few hospitals are therefore without some form of conventional equipment to monitor cardiac output.

The measurement of volumetric cardiac flow presents particular problems. First, the flow of blood in the vascular system is generally non-uniform. Second, the measurement device used should obviously not be more intrusive than necessary, not only to avoid reducing the accuracy of measurements but also to avoid interfering with the normal operation of the heart; otherwise, the measurement process itself may be more dangerous for a patient than any condition the measurement system is intended to discover. Third, the accuracy of measurement systems for cardiovascular flow suffers from the presence of often pronounced disturbances such as the pulsating nature of the flow and other disturbances such as are caused by the patient's breathing.

Because cardiac output is such an important diagnostic indicator, there are a large number of devices for measuring blood flow in the vascular system. In many passive measurement systems, some irregular indicator such as variations in optical translucence or magnetic irregularities are observed at two points in the blood vessel. Blood flow is then estimated as a function of blood velocity, which is in turn derived as a product of known auto- and cross-correlation techniques.

In active measurement systems, the indicator is injected into or is applied to the bloodstream, whereupon blood flow is determined by detecting the indicator downstream, integrating the time waveform of the detected indicator, and applying the assumption that the indicator is conserved. The indicators used in such systems include actual substances such as dyes and radioactive particles, and pure-energy indicators such as ultrasound and heat.

U.S. Pat. No. 4,236,527 (Newbower et al., 2 Dec. 1980) and U.S. Pat. No. 4,507,974 (Yelderman, 2 Apr. 1985), describe systems for measuring cardiac output in which heat is used as an indicator. In such heat-based systems, a balloon catheter is typically threaded down through the right jugular vein, and lodges proximal to the branch of the pulmonary artery via the right atrium and the right ventricle. The catheter includes a resistive heating element, which is positioned in the atrium and/or ventricle, and a thermistor, which is positioned in the artery.

In the Newbower system, the heating element is energized in such a way that the thermal energy applied to the surrounding blood has at least two frequency components, either a fundamental and one or more harmonics, or as a square-wave signal, which can also be resolved into a fundamental frequency and a number of harmonics. The temperature of the blood downstream is then measured by the thermistor and the corresponding electrical signal is filtered with respect to the fundamental frequency and at least one other frequency. Cardiac output is then estimated based on an approximate reconstruction of the transfer function of the local vascular system.

The Yelderman system energizes the heater according to a pseudo-random binary sequence (PRBS) of square waves that are derived based on a binary maximum-length sequence. Correlation techniques are then used to extract from the thermistor signal an estimate of the volumetric flow of blood from the heating element to the thermistor.

U.S. Pat. No. 5,146,414 (McKown, et al., 8 Sep. 1992) describes an improvement on the Yelderman system. In the McKown system, the transfer function of the channel (the region from where heat is applied to the blood upstream to the downstream position where temperature is sensed) is modeled, the approximate spectrum of the noise is determined, and the output of the system is used in a feed-back loop to adaptively update the parameters of the model and thus to improve the estimate of blood flow.

In U.S. Pat. No. 5,357,967 (Dixon, et al., 25 Oct. 1994) yet another heat-based system and method are described, in which the heat signal applied to the blood is in the form of a spread-spectrum signal, that is, it is a continuous signal with a continuously increasing or decreasing frequency. The signal sensed downstream is passed through a dispersive filter, from whose output signal an impulse response is determined. Blood flow is then calculated from the sensed impulse response.

A problem that arises in the context of all such methods of estimating cardiac output is that one must typically trade off speed of estimation against the accuracy and usefulness of the information one gets. If the patient's heart rate and flow are steady and even, the estimates from the monitoring equipment will be both accurate and timely, assuming the estimation routines they use are as well. Of course, most patients with such ideal heart parameters would not need to be monitored in the first place: monitored patients are often in the hospital or on the operating table for such procedures as by-pass surgery or because of problems involving the heart or pulmonary system.

In order to provide an accurate estimate of cardiac output (CO), one may use routines that generate estimates based on several consecutive heart cycles. The problem is, however, that such systems may be too slow to warn of a rapid decline in the patient's condition: a surgical team must know quickly if a patient's heart flow has just dropped by a large amount, since this may indicate a constriction that might be harder to detect using other equipment such as electro-cardiogram devices.

Recursive techniques such as the one described in McKown, for example, may give an accurate estimate of the general trend of cardiac output, but it may take too long for the system to settle on the trend value, and the trend value itself may not reflect accurately what is happening immediately. Yet other shortcomings of known recursive techniques for estimating cardiac output are that they require initialization and are not absolutely stable, that is, under certain circumstances, they may not converge at all to a useful estimate.

What is needed is therefore a device that not only provides accurate data about the general trend of a patient's cardiac output, but also about the more instantaneous or current flow state. There should preferably also be some way either to compensate for, or at least identify, potential instability in any recursive techniques that are used to generate output estimates.

SUMMARY OF THE INVENTION

The invention provides a method and a system for estimating blood output through a flow region of a patient's body, according to which an indicator, preferably heat, is injected as an indicator input signal with an input signal profile into an upstream position in the flow region. The preferred signal profile is a pseudo-random binary sequence. The presence of the indicator is sensed at a downstream position in the flow region as an indicator output signal. For a thermal indicator, this is preferably done using a thermistor. Cardiac output (CO) is then estimated in two separate estimators: a local estimator and a trend estimator. Both estimators estimate CO as a predetermined function of the input signal profile and the indicator output signal. The trend estimator forms its estimation based on data over a longer time frame than the local estimator. The invention thus provides estimated blood output values corresponding to both relatively fast and slow changes in blood output.

The trend estimator is preferably recursive. In the preferred embodiment the trend estimator is a Kalman filter.

A frequency-domain transfer function is preferably measured between the input and output signals for each period. The measured frequency-domain transfer functions thereby forms input signals for both local and trend output estimation.

The system advantageously determines optimal local state parameters as a predetermined optimization function of the transfer function model and the measured transfer function values, and the local estimator then estimates the local blood output value as a predetermined output function of at least one of the optimal local state parameters. The trend preferably estimates optimal trend state parameters by Kalman filtering the measured frequency-domain transfer function values, and estimates the trend blood output value as the predetermined output function of at least one of the optimal local state parameters.

The local and trend estimators cooperate to improve CO estimation accuracy and reliability. For example, the Kalman filter preferably is initialized using the optimal local state parameters.

The system preferably determines both an autocorrelation value Cxx of the input signal and converting the autocorrelation value Cxx to the frequency domain; and a cross-correlation value Cxy between the input signal and the output signal and converting the cross-correlation value Cxy to the frequency domain. It then computes the measured transfer function values as a predetermined function of the quotient between the frequency-converted cross-correlation and autocorrelation values.

The system according to the invention further includes a pre-filter that removes any low-frequency noise trend from the indicator output signals before local or trend estimation.

DETAILED DESCRIPTION

Figure 1:
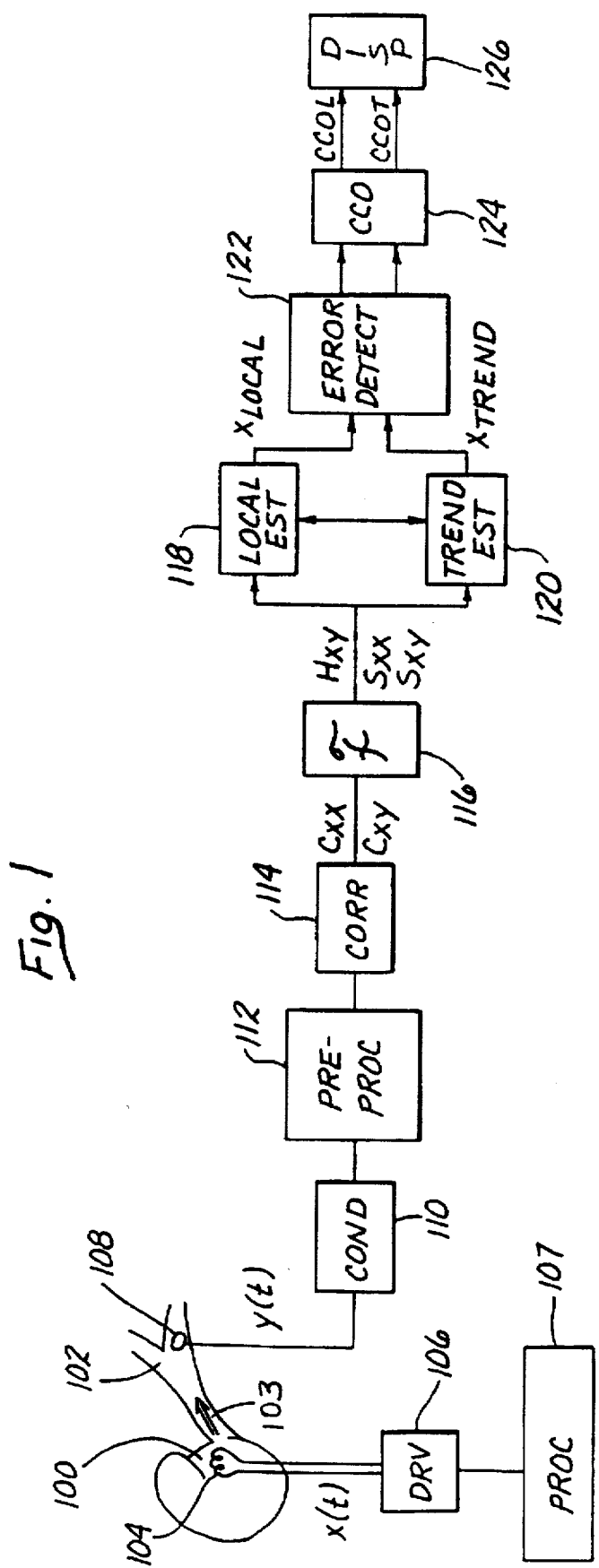
FIG. 1 is a block diagram that illustrates the main structural and functional components of a preferred embodiment of the invention in use for measuring cardiac output in a patient.

FIG. 1 is a generalized block diagram of the invention for measuring and displaying data about the cardiac output of a patient. A signal injection device is placed at an upstream position in the patient's cardiac system and a sensing device is placed at a downstream position. For accurate measurement of the cardiac output of a patient, it is advantageous to inject a signal into the blood in or near the patient's right atrium 100 and to sense the injected signal in or proximal to the branch of the pulmonary artery 102. These injection and sensing positions are therefore assumed below in order to illustrate the preferred embodiments of the invention. The flow of blood from the right atrium and toward the pulmonary branch is indicated in FIG. 1 by the arrow 103.

In order to avoid complications from injecting fluid or mass indicators, it is preferable to use a purely thermal heat signal as the basis of a measurement of the continuous cardiac output (CCO). In such case, heat is the injected indicator input signal, and the downstream temperature is sensed to provide an output signal upon which CCO estimates are based. An electrical heating element 104 is therefore positioned in the right atrium 100. The heating element 104 is preferably an electrically resistive element whose dissipated power (heat) is determined by the current or voltage supplied to the element via a driving circuit 106, which applies electrical current or voltage to the heating element 104 so that the dissipated power of the heating element 104 follows a predetermined signal profile x(t), which is generated by a processor 107.

Some examples of signal profiles that can be used in the invention are: a single or multi-frequency sinusoidal signal, such as is described in U.S. Pat. No. 4,380,237 (Newbower, 19 Apr. 1983); a spread-spectrum signal as described in U.S. Pat. No. 5,357,967 (Dixon, et al., 25 Oct. 1994); and a sequence of square-wave signals as described in U.S. Pat. No. 4,507,974 (Yelderman, 2 Apr. 1985). In the Yelderman system, the heat signal is generated according to a pseudo-random binary sequence (PRBS) and correlation techniques are used at the downstream position to extract the flow rate of the blood. The preferred embodiment of the invention uses such a PRBS heat signal as the injected input signal.

In the preferred case in which the injected signal is thermal, a thermistor or similar temperature-sensing element 108 is positioned at the downstream position in the pulmonary artery 102. If non-thermal indication signals are injected, then the thermistor will be replaced by an appropriate conventional sensor that detects the presence of the indicator downstream.

The thermistor is electrically connected to a signal-conditioning circuit 110, which may be any known circuit whose electrical output voltage or current is a known function of the temperature of the blood sensed by the thermistor 108. The signal-conditioning circuit 110 includes conventional circuitry for amplification and scaling of the sensed temperature signal, and also known analog-to-digital (A/D) circuitry to convert the continuous temperature signal y(t) to digital form for processing.

The heating element 104 and the thermistor 108 are preferably mounted spaced apart at or near the distal end of a catheter, which is then fed into a vein of the patient and threaded into and through the vein until the heating element and the thermistor reach their operating positions. This technique is well known and is therefore not described further.

The physical system defined by the heater element 104, the blood, the thermistor 108, and the circulatory system from the heater to the thermistor together constitute a "channel" through which heat signals propagate and are changed. Note that even the heater element and thermistor cause changes: the heater element cannot instantaneously change its output power and temperature to follow the PRBS pulses and the thermistor cannot perfectly track the continuous temperature changes in the blood that flows past it.

Conventional power and clock devices are preferably included to supply electrical power and timing signals to the driving circuit 106, processor 107, and the other components of the invention. These devices are neither illustrated nor described further since they are well known.

The signal conditioning circuit 110 is connected to preprocessor 112, which performs such functions as removing drift from the sensed temperature signal y(t) (preferably using a moving-average filter), and storing previous y(t) values in a memory buffer y_mem (not shown). The preprocessor 112 is connected to a correlation processor 114, which has as output signals the correlation profiles Cxx and Cxy, of the input signal x(t) with itself and with the sensed temperture signal y(t), respectively. The correlation processor's 114 output is connected as an input to a time-to-frequency domain or "Fourier" processor 116, which preferably performs Fourier transformation. The output signals from the processor 116 include a measured transfer function Hxy, as well as the frequency-domain representations Sxx and Sxy of Cxx and Cxy.

The preferred structure and function of the various processors 112, 114, and 116 are described in detail below. Any or all of these processors may be implemented as dedicated processors, for example using conventional high-speed digital signal processors (DSP's) or may be implemented in a single processor or processing system, including the processor 107.

The output signals from the Fourier processor 116, in particular, Hxy, are applied as input signals to two separate but cooperating estimators: a local estimator 118, and a trend estimator 120. These estimators, which also may be implemented using dedicated processors or within any other processor in the system, have as their primary output signals estimates X_local and X_trend of a state vector X, from which continous cardiac output can be determined. As FIG. 1 shows, however, the estimators also supply data to one another to improve their respective estimates. This is described below.

Both estimators 118, 120 thus generate estimates of cardiac output. In general, the local estimator 118 will generate stable estimates that more closely track rapid changes in cardiac flow than will the estimates of the trend estimator 120, which better tracks flow trends. The invention can thus operate in either, or preferably both, of two modes: 1) a "stat" mode, in which the user is given an early estimate of continuous cardiac output (CCO); and 2) a "trend" mode, in which the user is given information relating to longer term trends in CCO. The stat mode will be preferred for near real-time monitoring of a rapid cardiac output (CO) response, for example, following a drug titration, or the dynamic CO that occurs when a patient is coming off of cardiac bypass procedures. The trend mode is preferred for detecting a gradual change in CO due to, for example, fluid depletion, intravenous fluid addition, or the effect of a drug intervention. In the clinical setting, for example, an anesthesiologist during surgery will prefer the patient during time-critical surgical events. A physician on rounds, however, will generally prefer to see trend information since it better indicates more gradual changes in a recovering patient's status. The relative operation of the two estimators is also described in greater detail below.

The state estimates X_local and X_trend, as well as other signals (described below), are then input to error detection circuitry, which examines the signals to determine the presence of such disturbances as catheter disconnection, bolus injection, and electro-magnetic interference. If the error detection circuit detects such problems, then it signals the processor 107, the estimators 118, 120, or some other processor as needed to edit out faulty data, cause the system to reset, or some other recovery procedure. This is also descibed further below.

If no errors are detected, the state estimates are input to a CCO processor 124, which calculates both a short-term or "stat" CCO estimate CCO_l and a CCO trend estimate CCO_t. The formulas used by the CCO processor are discussed below.

Finally, the CCO estimates are applied as input signals to a standard display system 126, which displays the CCO values in any desired form.

In the preferred embodiment of the invention, thermal dilution of the blood is used to determine flow. In other words, one applies heat at an upstream position and then measures the blood temperature downstream to see how the blood has caused the input heat signal to change in between. Although, as is mentioned above, various heat signals may be applied successfully, the preferred heat signal is pulsed as described in Yelderman (U.S. Pat. No. 4,507,974), that is, it is applied as a pseudo-random binary sequence (PRBS), whose properties are well known. One advantage of the Yelderman method is that the spectrum of its input signal is "flat" (many frequency components of approximately the same amplitude over a given range) enough not to be "drowned out" in the noisy cardiac environment. Another advantage is that it is easy to adjust so as to better avoid noise frequencies (such as the strong component at ventilation frequency and its harmonics) by the noise frequencies typical in a patient—see McKown (U.S. Pat. No. 5,146, 414). Yet another advantage is that the PRBS signal lends itself well to detection using cross-correlation, and the cross-correlation function is itself useful for flow estimation.

Let $x=x(t)$ be the power applied to the heater element (as a PRBS), $y=y(t)$ be the measured blood temperature at the pulmonary artery, and $Cxy=Cxy(t)$ be the cross-correlation of x and y. Cross-correlation is a well-known concept that indicates how well two different signals "match up" at different relative time lags. Any known method may be used to carry out the cross-correlation calculations in order to determine the function $Cxy(t)$ given the known input power signal $x(t)$ and the measured temperature output signal $y(t)$.

Figure 2A:
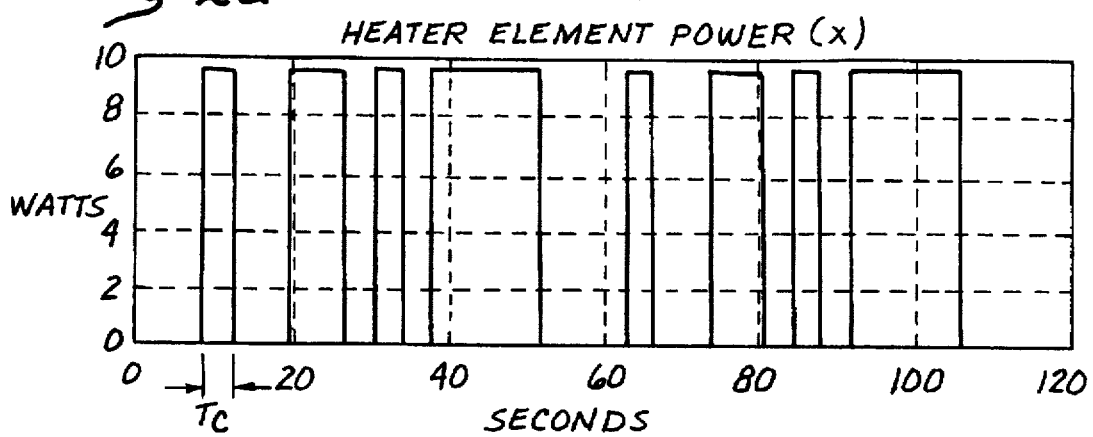
FIGS. 2(a), (b), and (c) illustrate, respectively the signal profiles of heater element power, thermistor temperature, and a cross-correlation (indicator dilution) curve for one test of the invention.
Figure 2B:
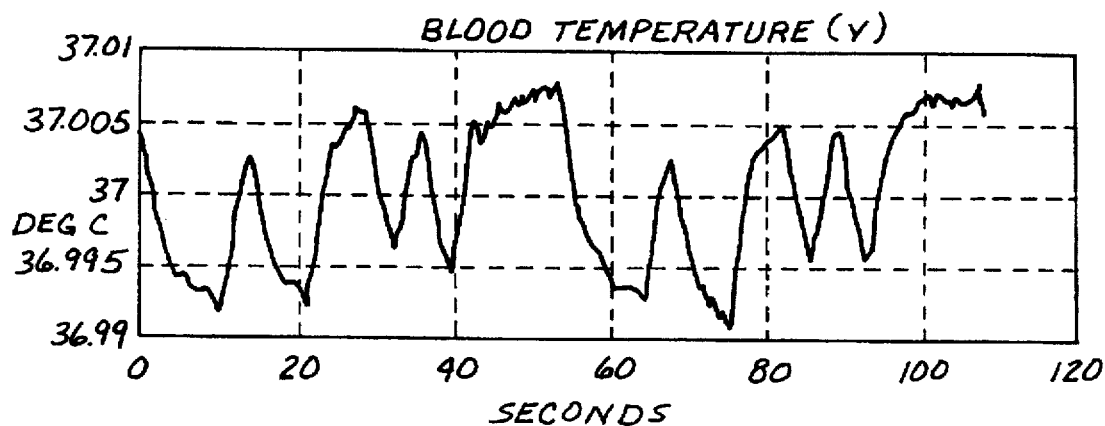
Figure 2C:
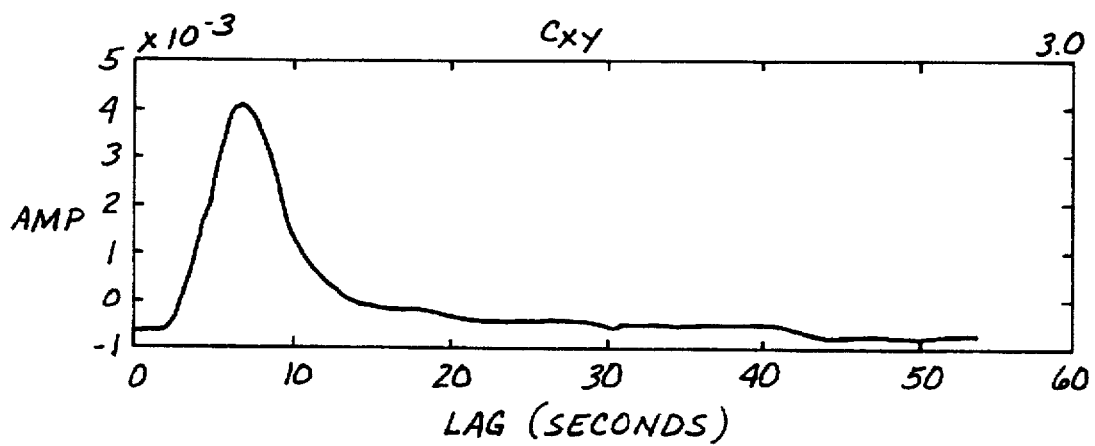
Figure 3A:
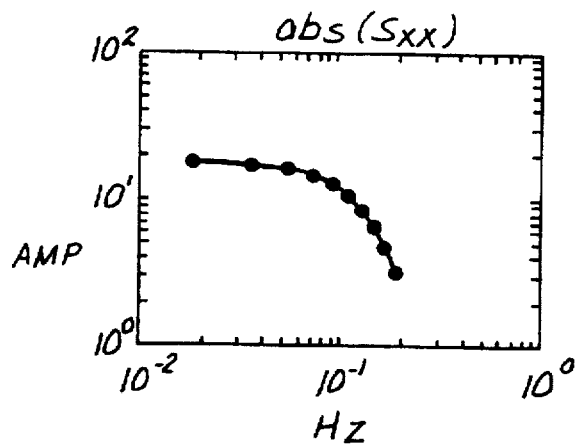
FIGS. 3(a)–(d) illustrate Bode plots of a frequency-domain representation of correlation data according to the invention.
Figure 3C:
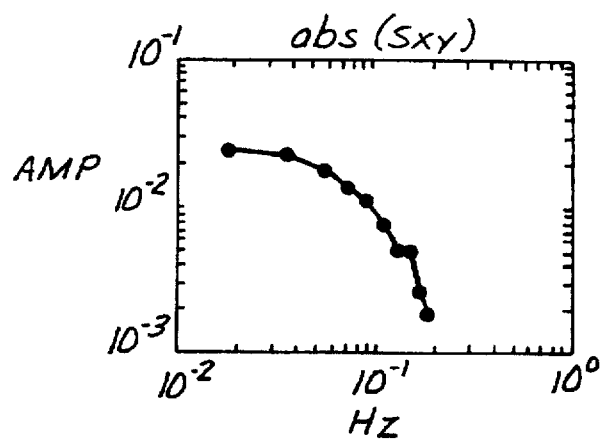
Figure 3B:
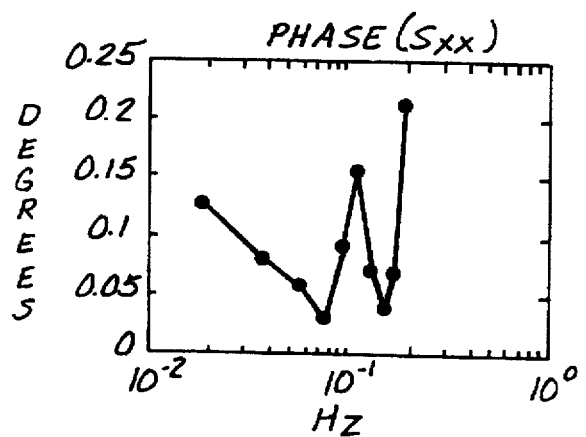
Figure 3D:
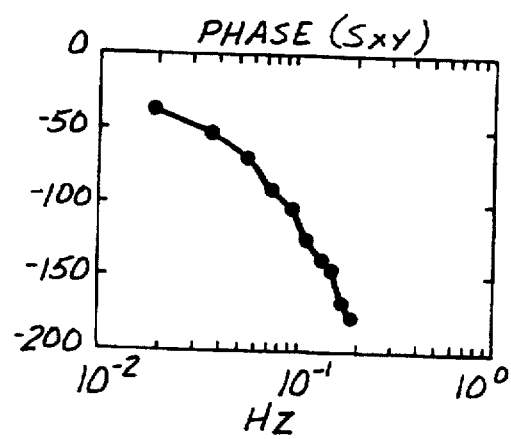

FIGS. 2(a)–(c) show, respectively, an example of two cycles of one such PRBS heater element power signal (x), the measured downstream pulmonary artery blood temperature signal (y) for the given PRBS signal x, and the cross-correlation function Cxy of these two signals.

As FIG. 2(a) shows, the PRBS signal is a series of pulses that have two states: ON, in which maximum power is applied (in the figure, about 9.5 W), and OFF, in which no power is applied. Each state lasts for a minimum pulse duration Tc, and the PRBS cycle lasts for and repeats after a predetermined number N of states. (The numbers N that create any of the preferred maximum length sequences can be determined using known formulae. In the illustrated example, N=15). As the figure shows, a PRBS does not just "toggle" back and forth between states after each time Tc, but rather state transitions follow defined patterns depending on the chosen number N.

Note that the peaks in blood temperature y occur about eight seconds after the corresponding peak in the input power signal, and that the peak in Cxy accordingly occurs for a lag of about eight seconds. Note also that the blood acts approximately as a low-pass filter of the input heat signal: y has roughly the same general shape as x, but with the sharp rises and falls "smoothed off". This is as one would expect, since the blood cannot be heated as rapidly as the heating element, and also since there is heat transport between regions of the blood as it flows toward the thermistor.

It can be shown theoretically (see, for example, the Yelderman patent) and confirmed by experiment that cardiac output (CO) is inversely proportional to the area under the cross-correlation curve Cxy. Thus:

$$CO = \frac{K}{AREA(Cxy)} = \frac{K}{\int_{t=0}^{s} Cxy(t)dt} \quad \text{Equation 1}$$

where s is chosen large enough tht the trybcatuib error is less than some predefined threshold and where K is a parameter that is proportional to the average heater power.

Since Cxy is calculated (for example, in the processor 114) and known before being input to either of the estimators 118, 120, one would at first think that two estimators are unnecessary: after determining the parameter K through calculation and calibration, one would have the value CO and thus the "answer" one is looking for. One problem is, however, in the clinical environment, the temperature data is typically too noisy to provide Cxy data that will integrate to a reliable estimate of cardiac output.

As is explained below, the invention uses the two different estimators to process a frequency-domain transfer function representation of the PRBS cross-correlation data. The inventors have discovered that by applying linear system identification theory and by further processing the sensed temperature data, more accurate trend information can be obtained as well as a short-term "stat-mode" estimate that can provide faster estimates for continuous cardiac output (CCO) monitoring.

One assumption that is common to all CO estimation techniques based on thermal dilution, including this invention, is that heat is conserved within the blood vessel. In other words, one assumes that the heat that the heating element 104 applies to the blood does not leave the blood, at least not until after it has passed the thermistor 108—the heat does not flow into or out through the walls of the blood vessel. It is known that this assumption holds good for physiological flows and for small temperature gradients between the blood and surrounding cardiovascular tissue.

Another common assumption is that the blood is well mixed by the right heart, at least by the time the blood reaches the thermistor. Together with the assumption of conservation of heat, this makes it possible to estimate the total system flow by measuring the associated temperature signal at any outflow for a flow system of otherwise arbitrary inflow-to-outflow structure.

Unlike other systems for estimating cardiac output, the invention uses to advantage one further assumption, namely, that the relationship between the heater element power and the pulmonary artery blood temperature is both linear and time-invariant. These two properties are commonly stated together as constituting a linear time-invariant system (LTIS).

The assumption that the channel is a linear system is reasonable since it implies that incremental input heat pulses relate proportionately to incremental output temperature wave forms, especially since the range of temperatures that are applied is limited: to heat the blood above about 50 degrees Celsius would in most cases cause tissue damage. The maximum heater surface temperature allowed in the preferred embodiment of the invention is 45 degrees Celsius, which is known to be safe. The assumption of time-invariance is also reasonable as long as changes in blood circulation occur slowly relative to the rate at which consecutive measurements of x and y are made.

Assume now that the applied heat signal is a PRBS wave form. The total heat energy in calories applied to the system during each PRBS cycle can be written:

$$\text{Heat\_in} = k_p \cdot \int_0^{N \cdot Tc} x(t)dt \quad \text{Equation 2}$$

where:

$k_p$=a predetermined heat unit conversion constant (=0.239 calories per second per Watt for unit conversion from Watts to calories);

Tc=PRBS state duration in seconds;

N=number of states per PRBS cycle;

t=time in seconds;

x(t)=the applied PRBS power signal (Watts) =P (maximum applied power) when the PRBS signal is ON and =0 when the PRBS signal is OFF.

The total heat energy flowing out of the system for each PRBS cycle can be written:

$$\text{Heat\_out} = k_f \cdot F \cdot d \cdot c \cdot \int_0^{N \cdot Tc} y(t)dt \quad \text{Equation 3}$$

where:

$k_f$=a predetermined flow conversion constant =1000/60 cm³ per second per liter per minute;

F=total system volumetric flow in liters per minute;

d=blood density=1.045 in grams per cm³;

c=specific heat of the fluid (blood)=0.87 calories per gram per degree Celsius); and y(t)=outflow temperature signal in degrees Celsius.

The assumption of conservation of heat in the steady-state means that Heat\_in=Heat\_out, or:

$$K' \cdot \int_0^{N \cdot Tc} x(t)dt = F \cdot \int_0^{N \cdot Tc} y(t)dt \quad \text{Equation 4}$$

where $K'=k_p/(k_f \cdot d \cdot c)$ is a conversion constant with units of degrees Celsius per Watt times liters per minute. For blood, with the given units, K'=0.0158. Note that a similar relationship can be derived in a known manner for any periodic power signal, for example, the multi-sinusoid input signal described in the Newbower patent, and the spread-spectrum input signals described in the Dixon et al. patent.

Now the assumption that the system is linear and time invariant (LTIS) means that the output y(t) is equal to the convolution of the input x(t) and the impulse response of the channel. As is well known, the impulse response function of a system describes the way in which the system responds over time to an instantaneous application of a unit of energy. As a simplified example, imagine that one were to strike a bell with a hammer with some unit of energy. The ringing of the bell (which lasts much longer—theoretically, infinitely longer—than the strike) would correspond to the bell's impulse response. If the bell were a perfect LTIS, then the frequencies of the ringing and their relative duration would perfectly characterize the bell itself.

In the context of the invention, $$y(t) = dc \cdot \int_0^{N \cdot Tc} h(s) \cdot x(t-s) ds \qquad \text{Equation 5}$$

where h(s) is the impulse response function of the channel and dc is the zero-frequency gain of the LTIS.

Therefore, (Equation 6):

$$K \cdot \int_0^{N \cdot Tc} x(t) dt = F \cdot \int_0^{N \cdot Tc} dc \cdot \int_0^{N \cdot Tc} h(s) \cdot x(t-s) ds dt$$

$$= F \cdot dc \cdot \int_0^{N \cdot Tc} ds \cdot h(s) \cdot \int_0^{N \cdot Tc - s} x(t) dt$$

Integration over one PRBS cycle yields the same number independent of the starting point, so that (Equation 7):

$$\int_{-s}^{N \cdot Tc - s} x(t) dt = \int_0^{N \cdot Tc} x(t) dt = \frac{P \cdot Tc \cdot (N-1)}{N}$$

This factor is common to both sides of Equation 6 and can therefore be factored out, leaving:

$$K = f \cdot dc \cdot \int_0^{N \cdot tc} h(s) \cdot ds$$

But since the integral over h(s) is unity, then $$F = \frac{K}{dc} \qquad \text{Equation 8}$$

which yields the desired relationship between the volumetric flow F (the CCO estimate) in liters per minute and the channel's LTIS direct-current gain, dc, in degrees Celsius per Watt.

The LTIS gain, dc, is the zero-frequency value of the channel's frequency response transfer function, Hxy(ω), which is defined as:

$$Hxy(\omega) = \frac{Y(\omega)}{X(\omega)}$$

where Y(ω) and X(ω) are the Fourier transforms of y(t) and x(t), respectively, that is:

$$Y(\omega) = \Im[y(t)] = \int_0^\infty y(t) \cdot e^{(-j\omega t)} dt$$

$$X(\omega) = \Im[x(t)] = \int_0^\infty x(t) \cdot e^{(-j\omega t)} dt$$

where ω=frequency in radians per second and $j=\sqrt{-1}$ $Y(\omega) = dc \cdot H(\omega) \cdot X(\omega)$ where:

$$H(\omega) = \int_0^\infty h(t) \cdot e^{(-j\omega t)} dt = \int_0^{N \cdot Tc} h(t) \cdot e^{(-j\omega t)} dt$$

Solving for the LTIS transfer function Hxy(ω) provides:

$$Hxy(\omega) = \frac{Y(\omega)}{X(\omega)} = dc \cdot H(\omega) \qquad \text{Equation 9}$$

Setting ω=0 (zero frequency) and recognizing that H(0)=1 identifies the LTIS gain parameter dc as the zero-frequency value of the system transfer function, that is, dc=Hxy(0).

This also gives one way of computing the system transfer function Hxy: sample the wave forms x(t) and y(t), then compute the discrete Fourier transform of each of the wave form using any known method to provide X(ω) and Y(ω), respectively, then do point-by-point division of these functions to give Hxy.

In the preferred embodiment of the invention, Hxy(ω) is determined as follows. First, x(t) and y(t) are individually cross-correlated with an ideal, zero-mean PRBS to produce the respective cross-correlation wave forms Cxx and Cxy. It can then be shown that:

$$Hxy(\omega) = \frac{Sxy(\omega)}{Sxx(\omega)}$$

where:

Sxx(ω)=ℑ[Cxx(s)]
Sxy(ω)=ℑ[Cxy(s)]
s is cross-correlation lag in seconds; and
ℑ indicates Fourier transformation.

In this method, the number of elements in the computed Cxx and Cxy vectors is equal to the number of samples in one period (PRBS cycle) of the x and y data waveforms. This number, the samples per run (SPR) is:

SPR=N*Tc*Fs where
N=the number of states in the PRBS
Tc=time duration of each state in seconds; and
Fs=the number of samples per second, that is, the sampling rate.

For typical values such as N=15, Fs=10, and 2≦Tc≦4, then SPR ranges from 300 to 600. In systems such as McKown's, Tc is adjusted in increments of 0.1 seconds in order to improve system performance by avoiding frequencies that contain large noise components.

Figure 4A:
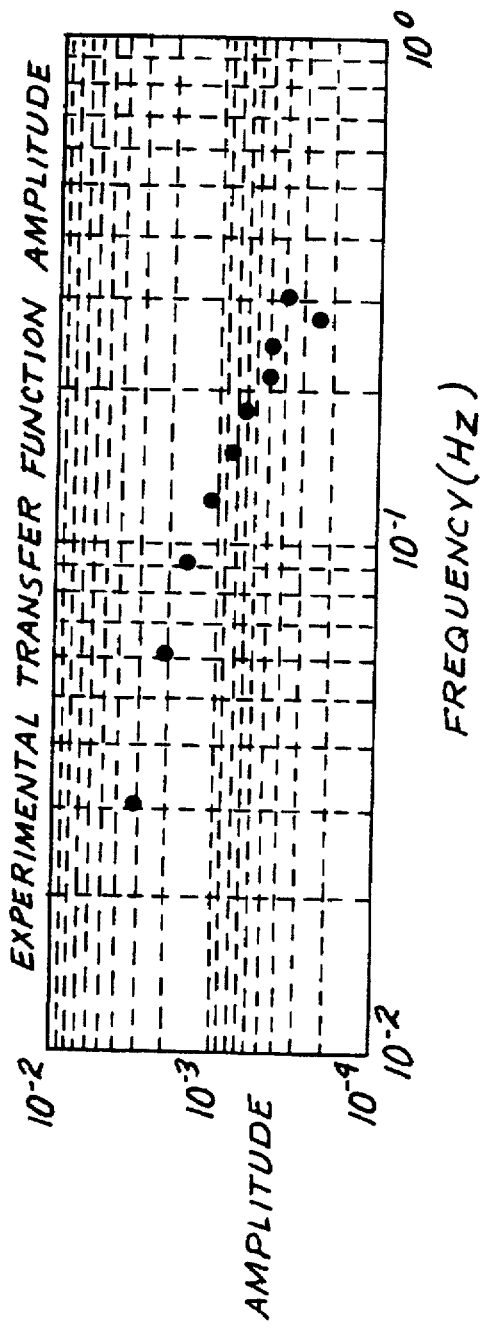
FIGS. 4(a) and (b) show a Bode plot of transfer function data with a high signal-to-noise (SNR) ratio.
Figure 4B:
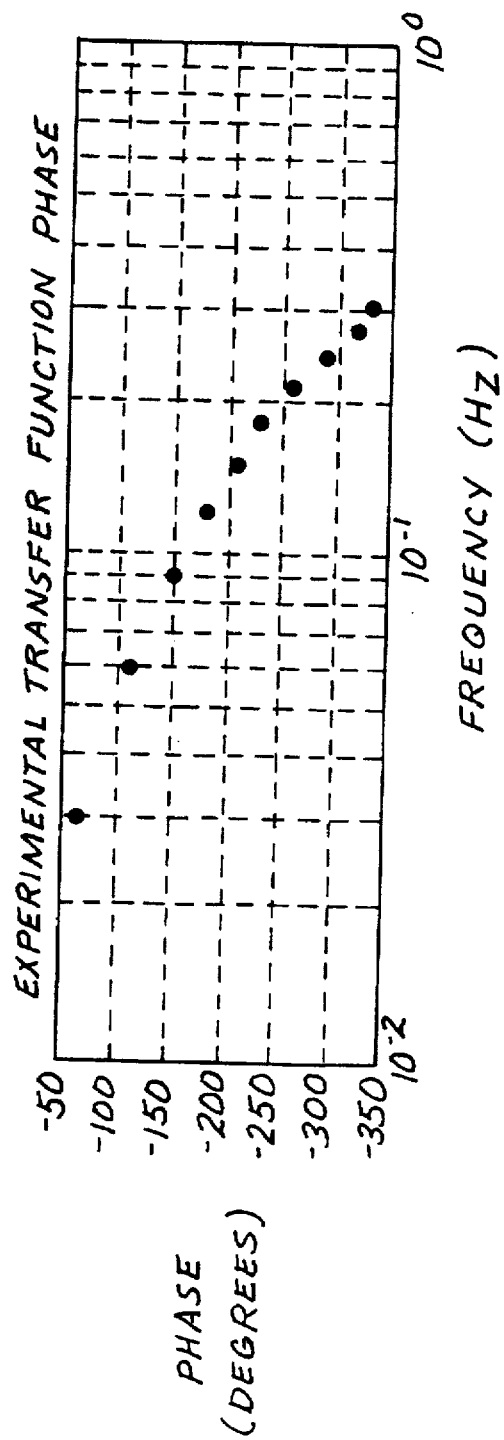

FIGS. 3(a)–(d) show standard Bode plots of Sxx and Sxy in one actual test. Note that Sxx is essentially zero-phase. FIGS. 4(a),(b) show the corresponding Bode plot of the measured transfer function Hxy, which was computed as the ratio of Sxy and Sxx.

In practice, the inventors have determined that it is sufficient to measure Hxy only at the frequencies where $X(\omega)$ has significant power, that is, at the most dominant frequencies of the heat input signal $x(t)$. For a PRBS input these are the lower harmonic frequencies located at $\omega_n = n/(N*Tc)$ for $n=1, 2, \ldots$ m. In tests the inventors have found $m=10$ to be sufficient, but more or fewer than ten frequencies may be included; the actual number may be determined using conventional simulation and experimentation. By way of example only, it is assumed that $m=10$ below.

This means that the transfer function Hxy can be adequately determined by only m complex numbers (each of the frequencies is complex) $Hxy(\omega_n)$, which categorize the relationship between the power signal x and the temperature signal y. This represents a great computational saving compared with the 300–600 complex numbers required just to represent each of the functions Cxx and Cxy.

Characterizing the input-output relationship based on the transfer function Hxy rather than on the area under the cross-correlation curve Cxy has at least the following advantages:

1) Efficiency of representation: only ten complex numbers are required instead of the 300–600 (or whatever SPR is for a given application) for Cxy.

2) Noise whitening: the noise is often almost uncorrelated between the elements of Hxy but is highly correlated between the elements of Cxy.

3) Baseline subtraction: using the transfer function inherently avoids the problem of estimating the baseline of Cxy, which is difficult in the presence of such low-frequency noise as is normally found in the cardiac environment.

4) Efficiency of mathematical modelling and analysis: the transfer function approach allows a simple Fourier transform representation of the preferred LTIS model for indicator dilution. This has the added advantage that it allows the use of particularly robust routines for estimating the parameters of the chosen model.

As Equation 9 and its development imply, if the unity gain transfer function $H(\omega)$ or the impulse response $h(t)$ were known, then each single one of the ten respective complex numbers would be sufficient to provide an estimate of the steady-state gain, dc, as follows:

$$dc(n) = \frac{Hxy(\omega_n)}{H(\omega_n)} \quad \text{for } n = 1, 2, \ldots, 10$$

Each estimate of dc would then provide an associated estimate of cardiac output by dividing dc into K', according to Equation 8. The problem is that before one can get to this point, one must have some idea of the shape of the indicator dilution curves which, given the LTIS assumption, determine both $h(t)$ and $H(\omega)$.

In the context of estimating cardiac output, the "lagged normal model" described by Bassingthwaighte, et al. in "Application of Lagged Normal Density Curve as a Model for Arterial Dilution Curves," Circulation Research, vol. 18, 1966, has proven to be particularly accurate and useful, and it is therefore the preferred model for cardiac output according to the invention. In this discussion, the lagged normal model is defined as an LTIS whose impulse response is the convolution of a unity-area Gaussian (normal distribution) function and a unity-area decaying exponential. The Gaussian has two parameters: the mean $\mu$ and the standard deviation $\sigma$. The exponential has one parameter: the time-decay parameter $\tau$. The unity-gain, lagged-normal transfer function H_ln at each frequency $\omega$ thus depends on $\mu, \sigma,$ and $\tau$ as follows:

$$H\_ln(w|\mu, \sigma, \tau) = \frac{e^{(-j\omega\mu - (\omega\sigma)^2/2)}}{(1 + j \cdot \omega \cdot \tau)} \quad \text{Equation 10}$$

The physical meaning of these parameters is:

$\mu$: a pure time delay that represents translational flow;

$\sigma$: a measure of random dispersion $\tau$: a time constant associated with mixing in a distribution volume, which, in this example, is the blood vessel.

The units of $\mu, \sigma,$ and $\tau$ are time (seconds).

If $\mu, \sigma,$ and $\tau$ were known, then each of the ten complex measured numbers $Hxy(\omega_n)$ would individually provide an estimate of cardiac output (CO) according to:

$$CO(n) = \frac{K' \cdot H_{ln}(\omega_n)}{Hxy(\omega_n)} \quad \text{for } n = 1 \text{ to } 10 \quad \text{Equation 11}$$

In order to apply this relationship, however, one must first determine not only what the values of $\mu, \sigma,$ and $\tau$ should be, but also how the ten cardiac output estimates should be combined.

One should note that the cardiac output does not depend on the shape of $h(t)$, $H(\omega)$, or $Hxy(\omega)$, but only on the LTIS zero-frequency gain, dc. Since the experimental transfer function Hxy is measured at ten frequencies $\omega_n$ that are not zero, however, it is also necessary to estimate the unity gain transfer function $H(\omega_n)$ in order to extrapolate the measured $Hxy(\omega)$ to zero frequency. Assuming the lagged normal model, this means that one must estimate the "shape" parameters $\mu, \sigma,$ and $\tau$ in order to estimate the gain parameter dc.

The first step in estimating $\mu, \sigma,$ and $\tau$ is to measure the power-to-temperature frequency domain transfer function $Hxy(\omega_n)$, at its first ten harmonics. The second step is then to analyze these measurements with the aid of the theoretical lagged normal model for the transfer function data.

Let $X = [dc, \mu, \sigma, \tau]$ be the vector of parameters to be estimated. Then:

$$Hxy\_ln(\omega|X) = dc * H\_ln(\omega|\mu, \sigma, \tau)$$

The next step is to estimate the state vector X such that $Hxy\_ln(\omega_n|X)$ describes all ten $Hxy(\omega_n)$ measurements optimally in some sense. The definition of what is "optimal" is a matter of design choice, but the preferred definition according to the invention is that the sum of the squared error is minimized; this choice makes possible the use of particularly advantageous estimation routines, as is described below.

Figure 5A:
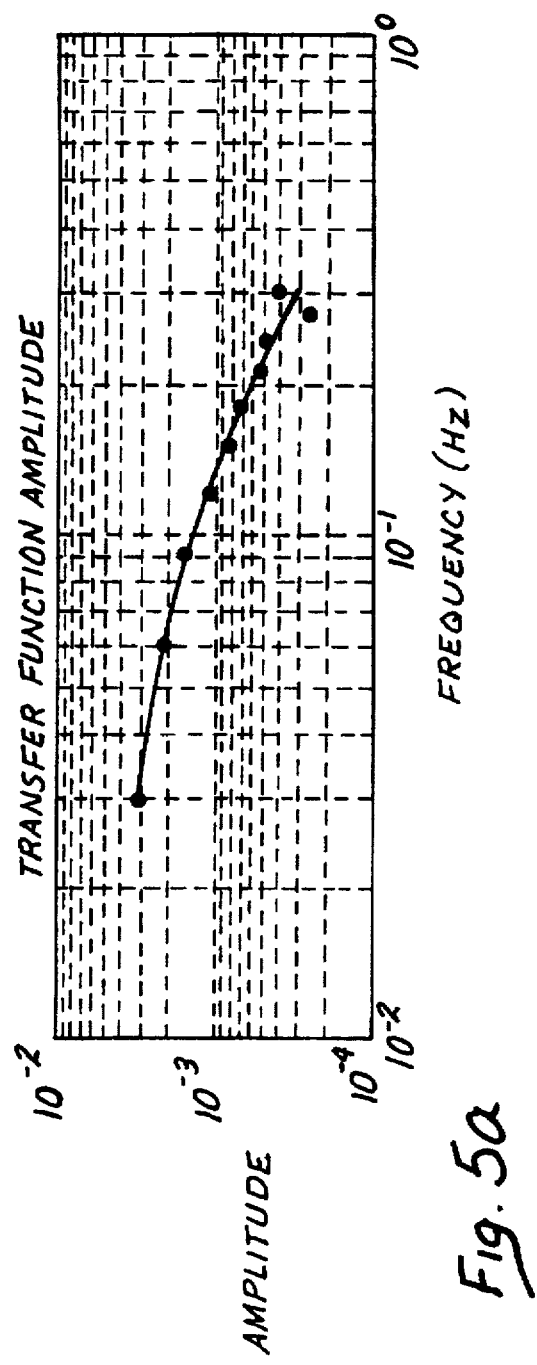
FIGS. 5(a) and (b) illustrate a Bode plot that compares measured transfer function data with a transfer funciton model used in a preferred embodiment of the invention.
Figure 5B:
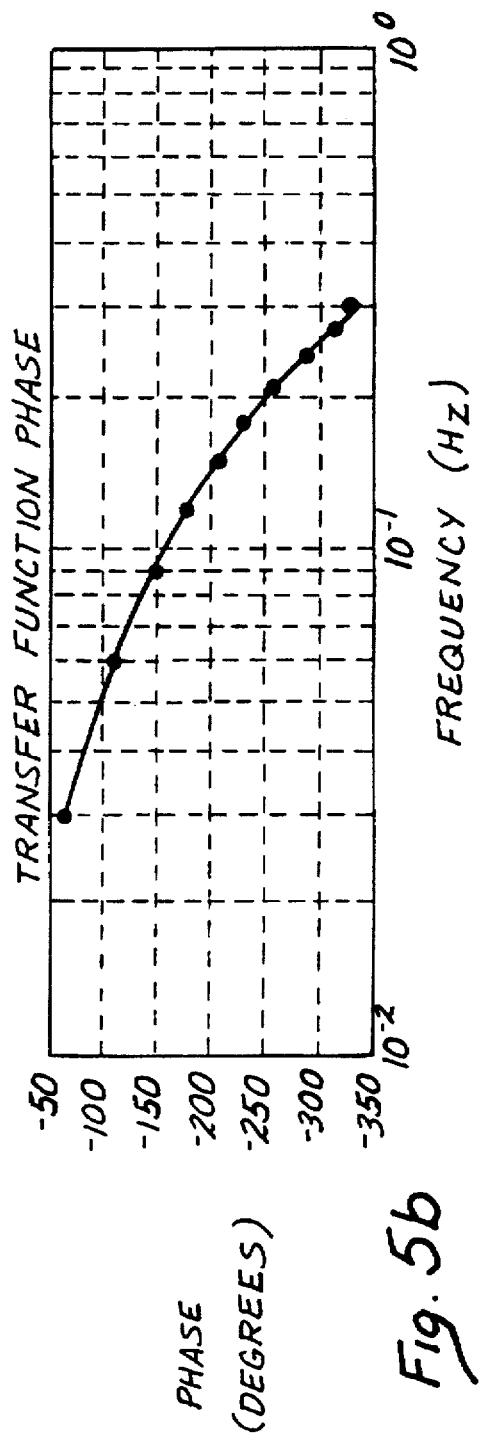

FIGS. 5(a),(b) illustrate how well the transfer function data (plotted as data points) of FIGS. 4(a), (b) can be fit using the lagged normal model $Hxy\_ln(\omega|X)$. In this actual test, the system defined as the patient's catheter, right heart, and pulmonary artery was well characterized by the parameter vector $X = [dc, \mu, \sigma, \tau] = [0.0040° \text{ C.}, 2.4 \text{ s}, 0.6 \text{ s}, 4.0 \text{ s}]$. For these values, the estimate of the patient's cardiac output is then $0.0158/0.0040 = 3.9$ l/min. The manner in which the parameters are determined is described below.

A useful analytical form of the unity gain impulse response for the lagged normal model is:

$$h\_ln(t|\mu, \sigma, \tau) = \quad \text{(Equation 12)}$$

$$\frac{1}{2\tau Fs} \cdot e^{\left(\frac{-(t-\mu)}{\tau} + \frac{\sigma^2}{2\tau^2}\right)} \cdot \left\{ \text{erf}\left(\frac{t-\mu-(\sigma^2/\tau)}{\sigma\sqrt{2}}\right) + \text{erf}\left(\frac{\mu-(\sigma^2/\tau)}{\sigma\sqrt{2}}\right) \right\}$$

where erf() is the known error function and t is time in seconds.

This expression for h__ln allows the lagged normal model to be readily evaluated based on cross-correlation as well as in the frequency domain. Once again, assuming the system is an LTIS, it can be shown that:

$$Cxy\_model(X) = dc \cdot h\_ln(t,\mu,\sigma,\tau) \otimes Cxx$$

where $\otimes$ denotes convolution. Tests by the inventors have shown very close agreement between the modelled cross-correlation function Cxy_model and measured Cxy data for the same patient and lagged normal parameters as in FIGS. 5(a),(b).

The inventors have also found empirically that the dispersion parameter $\sigma$ is often poorly determined from the observed Cxy or Hxy data. In clinical tests for which the signal-to-noise-ratio (SNR) was high enough to determine $\sigma$, the inventors found that $\sigma$ was linearly related to $\tau$. For other patients, the linear relationship $\sigma = a \cdot \tau + b$ can be established and quantified using known methods. In one test of 100 patients, the inventors observed the relationship $\sigma = 0.26\tau - 0.5$; this result was also in qualitative agreement with the findings of Bassingthwaighte, et al.

If one assumes a linear relationship between $\tau$ and $\sigma$, then one need only estimate one parameter in order to have estimated both. In the preferred embodiment of the invention, the processor estimates $\tau$ because it is associated with the corner frequency of the transfer function. (It is also possible to estimate $\sigma$ and then compute $\tau$, although $\tau$ is the more clearly identifiable feature of the transfer function.) It is then possible to reduce the lagged normal parameter vector X by one parameter, so that $X = [dc,\mu,\tau]$.

The problem then remains to estimate this parameter or "state" vector X. According to the invention, two complimentary estimation routines are used: SNR-dependent, local, signal-averaging estimation in the local estimator 112; and trend estimation based on "raw," that is, unaveraged, transfer function observations. Note that an accurate estimate of X is all that is needed, along with the assumptions stated above (such as LTIS), to generate an estimate of the dc gain, and thus of the cardiac output.

As is stated above, the lagged normal model, which is characterized by the parameter vector $X = [dc,\mu,\sigma,\tau]$, has proven to describe the transfer function for cardiac flow very well. Assuming conservation of heat and that the channel is an LTIS, however, the invention may be used with any other suitable model of the cardiac transfer function that can be characterized by a parameter vector X.

Local Estimation

The problem of accurately estimating X is equivalent to the problem of finding a lagged normal transfer function model Hxy__ln($\omega_n$|X) that approximates the observed, measured transfer function in some predetermined sense. The difference between the modelled and the measured transfer functions can be quantified by a cost function, whose values depend on the choice of X. In the preferred embodiment of the invention, the local estimator 118 evaluates and minimizes the following cost function Hxy__cost(X):

$$Hxy\_cost(X) = \sum_{n=1}^{10} [Hxy\_SAE(\omega_n|x) \cdot W(\omega_n)] \quad \text{(Equation 13)}$$

where $$Hxy\_SAE(\omega_n|X) = |[Hxy\_avg(\omega_n) - Hxy\_ln(\omega_n|X)|^2$$

is the squared absolute error (SAE) of the average measured transfer function Hxy__avg($\omega_n$) relative to the lagged normal transfer function model Hxy__ln($\omega_n$|X) at the PRBS harmonic frequencies $\omega_n$ given the state vector $X = [dc,\mu,\tau]$ (if reduced). Each squared absolute error value is preferably weighted with the weights W($\omega_n$); this is the same as forming the weighted least-squares approximation.

Notice that the measured transfer function values Hxy__avg($\omega_n$) are preferably averaged. The preferred method of averaging is described below.

Although the weights W($\omega_n$) may be chosen using normal simulation and experimentation, they are preferably set as follows:

$$W(\omega_n) = \frac{Sxx(\omega_n)}{R\_Hxy(\omega_n)}$$

where Sxx($\omega_n$) is the heater element power at $\omega_n$ and R__Hxy($\omega_n$) is the statistical variance of Hxy($\omega_n$). The heater element power can be determined beforehand at any given frequency using standard methods of measurement and analysis.

To obtain R__Hxy($\omega_n$), one should first note it is also the observation noise power, which is discussed in more detail below. This value may be obtained from the "raw" data using the trend estimator. (It is the n'th diagonal element of an observation noise covariance matrix, which is described below.) The advantages and other properties of the preferred cost function, shown above, are discussed in the well-known text, *System Identification for the User*, Lennart Ljung, pp. 173–75, Prentice Hall, 1987.

The value of the three-element vector X that minimizes the cost function Hxy__cost(X) for the complex transfer function measured at ten frequencies $\omega_n$ may then be used directly to calculate dc and thus CO. Minimizing Equation 13 over X for ten frequencies involves a non-linear least-squares minimization, and there are several well-known methods for performing this optimization. Examples of such methods are the many gradient descent methods, including Newton-Raphson-type routines. Because of guaranteed convergence, the method preferred in the invention is the Nelder-Mead simplex routine, which is a well-established numerical method for searching a parameter space to minimize a function of the parameters.

The simplex routine is non-recursive. It provides a parameter vector X that best fits the lagged normal model to the measured data without needing any previous estimate of X. It can thus rapidly produce a value of cardiac output. On the other hand, the accuracy of this rapid value depends on how noise-free the measurement data Hxy__avg is. Since the raw data Hxy is typically very noisy, the measured values should preferably be averaged to at least reduce the impact of noise before they are used in the simplex routine to generate CO values.

According to the invention, the input to the simplex routine is preferably a weighted average Hxy__avg of a predetermined number N__t of the most recent transfer function measurements Hxy. Because the transfer function includes phase as well as amplitude information, the signal averaging preferably uses a weighting function that is inversely proportional to the square root of the noise power. Similarly, a weighted average of the measured cross-correlation values Cxy__avg is computed. Thus:

$$Hxy\_avg = \sum_{m=1}^{N_t} \frac{H_{xy_m}}{\sqrt{v_m}} \quad \text{and} \quad Cxy\_avg = \sum_{m=1}^{N_t} \frac{C_{xy_m}}{\sqrt{v_m}}$$

where $v_m$ is the noise power for the m'th measured transfer function. The preferred way in which noise power is computed is described below.

One advantage of the local estimator is that it is self-initializing: a CO value can be determined from a single Hxy measurement. Yet another clear advantage is that it provides estimates quickly, and is thus well suited for use in the "start mode." Still another advantage is that the local estimator is always stable: no combination of measured transfer function values Hxy can cause the estimator to diverge and fail, since even an extremely noisy or erroneous value will "disappear" completely from all calculations in the time it takes to input the number of measured transfer function values used in the average (which may be only one value).

One drawback of the local estimator, however, is that the local CO estimates are noise-dependent. The local estimator takes values as they are presented, noise and all, and the best that the local estimator can do to counteract noise is to apply weighted averaging in order to reduce its effect. Weighting helps, of course, but in order to weight the average in some useful way, one must have an estimate of noise power. The preferred method of calculating the noise power estimate is described below.

Another shortcoming of the local estimator is that it is not self-verifying: it gives no indication of whether the currently calculated CO value "makes sense" in the light of previous values, since it does not consider any trends. Unless averaging is included, it contains no "memory," and if averaging is included, then its memory is still short-term.

Trend estimation

One way to increase the "memory" of an estimator is simply to include in the estimation many more previous values of Hxy, with appropriately chosen weights for averaging. In other words, one may implement the trend estimator 120 using a known non-recursive block-averaging filter or an FIR (finite impulse response) filter that uses enough previous values of Hxy. Conventional experimentation and design techniques must then be applied to choose the filter coefficients to reduce the effect of expected noise and to provide a CO value that has been averaged in a way that experiments show to be sufficiently useful as an indication of a CO trend. If such an FIR implementation is chosen for the trend estimator, then it should include at least two times as many previous values of Hxy as are used in the weighted averaging for the local estimator, and preferably four times as many, in order to reduce even further the effect of noise.

At the cost of potential instability, an infinite impulse response (IIR) filter may also be used to implement the trend estimator. Conventional techniques may be used to select its coefficients. One of several problems with such FIR and IIR arrangements is that they, too, provide no indication of noise; rather, they assume that one has taken anticipated noise frequencies into account when selecting their coefficients.

According to the invention, the trend estimator 120 is preferably a recursive estimator. One example is a known recursive LQ least-squares estimator. The preferred implementation of the trend estimator according to the invention is, however, a Kalman filter.

There are several advantages to a Kalman filter implementation, which include: 1) a Kalman filter does not require pre-input signal averaging—the Kalman filter can thus operate directly on "raw," noisy data; 2) the Kalman filter estimates noise, and adjusts its gain "automatically" as noise increases—as long as certain general assumptions about the distribution of the noise power are satisfied, the user does not need to "know" what the noise is in the channel in order to reduce its effect; 3) using certain modifications according to this invention, the length of the Kalman filter's exponentially decaying memory can be adjusted depending on the noise in order to allow an adjustable trade-off between the speed (responsiveness) and accuracy of the estimate of the CO trend; and 4) the local estimate can be used to offset the effects of the possibility that the Kalman filter will diverge for a patient with a high SNR. The general structure of the Kalman filter, its use and advantages are described more fully below. For a fuller description of the theory and properties of classical Kalman filters one may consult any of a large number of known texts, such as *Applied Optimal Estimation*, Arthur Gelb, TASC, M.I.T. Press, 1989.

Given the sequence of transfer function measurements Hxy for the assumed LTIS, which is defined by the input power signal x(t) and the output temperature signal y(t), the trend estimator recursively estimates the parameter vector X=[dc,μ,τ], which in turn defines the transfer function Hxy_ln(ωlX) of the lagged normal model of Hxy. This allows the system's direct current gain, dc, and thus the cardiac output, to be estimated from what are essentially alternating current electrical measurements.

The problem of determining X can be stated in terms of a discreet time system model equation and an associated measurement model equation. Time will be expressed in units, such that time t=(n+1) is one time unit after time t=n. The time unit in the following equations is the time between generation of two successive measurements of the Hxy of the transfer function.

$$X(n)=X(n-1)+X\_rw \quad \text{(system model)}$$

$$Hxy=Hxy\_ln(X(n))+H\_on \quad \text{(measurement model)}$$

where:

X(n) is the present value of the state (parameter) vector $[dc,\mu,\tau]^T$;

X(n−1) is the most recent previously determined value of;

X_rw is a 3-element vector defining a random walk for X;

Hxy is the most recently observed transfer function;

Hxy_ln(X(n)) is the transfer function of the lagged normal model using the present value of X; and H_on is the present transfer function of observation noise.

For m=10, Hxy, Hxy_ln(X) and H_on are 10×1 complex vectors with an element for each of the first ten PRBS harmonics.

The system model according to the invention introduces the random walk term X_rw into the model. This term violates the assumption that the system is linear and time-invariant (LTIS) and is not necessary to the invention; it is useful, however, for controlling the responsiveness of the CCO estimation routine according to the invention and its inclusion is therefore preferred. The LTIS assumption can be interpreted as requiring the variance of the elements of X_rw to be kept so small that the system changes at most slowly.

The system model used in the invention involves a time-domain estimation of frequency-domain parameters. Classical Kalman filter theory provides a well-motivated approach to time-domain recursive estimation provided that the system and measurement model equations are linearly related to all elements of the state vector; the observation noise is stationary; and the observation noise obeys uncorrelated Gaussian statistics. If these conditions apply, then the Kalman filter can be shown to provide optimal estimates of the parameters in the state vectors in the sense of giving the minimum mean-squared error (MMSE). None of these three conditions apply strictly in the preferred embodiment of the invention, but the problems that may arise because of the differences are addressed according to the invention in such a way that the trend estimator can still be implemented using Kalman filtering techniques to give accurate estimates.

First, an extended Kalman filter is used in the invention in order to deal with the problem of parameter non-linearity. Second, the problem of non-stationary observation noise is dealt with by making the Kalman filter control parameters and the estimates of the noise covariance-adaptive. Third, a "Gaussian editor" is included in the preferred embodiment of the invention in order to adjust for the observation noise not having a Gaussian amplitude distribution. These extensions and modifications of the trend estimator are discussed below.

Observe that the lagged normal transfer function measurement model Hxy__ln($\omega$|X) is linear with respect to the dc parameter but is non-linear with respect to $\mu$ and $\tau$. It has, however, continuous derivatives with respect to all three parameters, which is required theoretically in order to use an extended Kalman filter. This is established in such standard texts as *Applied Optimal Estimation*, which is referenced to above.

The following Kalman filtering equations define the first-order extended Kalman filter according to the invention for the system and measurement model equations given above: Kalman gain matrix:

$$L = \text{SIGMA} \cdot dHdX' \cdot [dHdX \cdot \text{SIGMA} \cdot dHdX' + R\_Hxy]^{-1}$$

State vector update:

$$X(n) = X(n-1) + Re\{L \cdot [Hxy - Hxy\_\ln(X(n-1))]\}$$

Note that [Hxy−Hxy__ln(X(n−1))] is the error between the actually observed and predicted values of the transfer function. The initial value for X, that is, X(0), is preferably set to the first value of X calculated by the local estimator. In practice, the first three values of X are preferably set equal to the values determined by the local estimator, since at least three values for Hxy are preferred to be available before the trend estimator calculates the variance estimate R__Hxy. Covariance matrix update:

$$\text{SIGMA}(n) = \text{SIGMA}(n-1) - Re\{L \cdot dHdX \cdot \text{SIGMA}(n-1)\}$$

To form a starting value for SIGMA, the system set the i'th diagonal element of SIGMA (off-diagonal elements are set to zero) to ($\sigma\_\text{init} \cdot X_0(i))^2$ where $\sigma\_\text{init}$ is an experimentally determined, preset initial standard deviation factor (in one prototype, $\sigma\_\text{init}=0.15$) and $X_0$ is the first estimate of $X=[dc,\mu,\tau]$ calculated by the self-starting local estimator. At each iteration, the covariance matrix is extrapolated according to the following preferred covariance matrix extrapolation:

SIGMA is set to $f$SIGMA+$Q$

In these expressions,
- · indicates vector/matrix multiplication;
- ' denotes vector/matrix (conjugate) transposition;

Re{.} indicates the real part of the argument;

SIGMA is the real 3×3 error covariance matrix for X;

L is the complex 3×10 Kalman gain matrix;

R__Hxy is the 10×10 real diagonal, noise variance matrix for Hxy, which may be calculated using any conventional routine based on a predetermined number of previous values of Hxy;

dHdX is the complex 10×3 derivative (Jacobian) of Hxy__ln($\omega$|X) with respect to X;

f is a real fading-memory scalar (f>1); and

Q is a real 3×3 random walk covariance matrix.

Remaining terms are defined above. These terms and their effect on the estimation routine are known in the art.

These filter equations are implemented in the processing system and recursively estimate both the state vector X and the state vector covariance SIGMA. In this context, the term "update" refers to the portion of the recursive estimation cycle that is based on a new observation, whereas the term "extrapolation" refers to the portion between observations.

Between observation, it is assumed that the expected value of X remains constant. This is consistent with both the LTIS assumption and the random walk modelling construct, since the expected value of any element of the random walk vector X__rw is zero.

The frequency dependency of the Kalman filtering equations is implicit: The experimentally observed transfer functions Hxy and the lagged normal transfer function model Hxy__ln(X) both consist of ten complex numbers, one for each of the first ten harmonics of the PRBS power signal. Each element is thus given as:

element{Hxy}=Hxy($\omega_n$)=observed transfer function at $\omega_n$; and element{Hxy__ln(X)}=Hxy__ln($\omega_n$,X)=model transfer function at $\omega_n$=2$\pi$·n·(Fs·SPR) for n=1 to 10, where, as before, Fs is the number of samples per second and SPR is the number of samples per PRBS run.

The derivative matrix dHdX consists of three columns defined by the derivative of Hxy__ln($\omega_n$,X) with respect to each of the elements of X and ten rows for the value of each derivative at the ten values of $\omega_n$. The n'th row of dHdX is therefore given by:

$$\left[ \frac{1}{dc}, -j \cdot \omega_n, \frac{-j \cdot \omega_n}{1 + j \cdot \omega_n \cdot \tau} \right] \cdot Hxy\_\ln(\omega_n | X)$$

As the state vector update equation shows, the system decides how much X has changed from one observation to another based on two factors: the Kalman gain matrix L, and the difference between what the system just measured the transfer function to be (Hxy) and what it was "expected" to be according to the lagged normal model Hxy__ln(X). In other words, the more the model deviates from "reality," the farther off the system assumes its estimated X to be, and the more it is changed. The gain matrix determines how much weight each deviation is given. If the gain is zero, or the model agrees exactly with the observation, then the system continues to assume that the most recent estimate of X is the best.

The error covariance matrix update is less intuitive in that it contains two modelling constructs—f and Q—that govern the gain of the Kalman filter, which in turn governs the responsiveness of the CCO estimate to changes in cardiac output.

The scalar fading memory parameter f is defined as f=exp(1/N__fade), where N__fade is a positive integer that represents a number of PRBS runs. N__fade may be predetermined by experiment and preset in the system, but it is preferred that it be adjustable based on the block size of the local estimator and an estimated signal-to-noise ratio; this is described in greater detail below. Inclusion of the term N__fade forces the recursive estimation process to exponentially "forget" data in the past, that is, it determines how quickly the contribution of a given observation to influence the calculations will decrease.

The random walk covariance matrix Q is a real 3×3 diagonal matrix, whose diagonal elements represent the variance of the elements of the random walk vector X_rw. The variance of such random variables is easily computed using known techniques. The system generates the random walk vector itself, as is described below.

As the Kalman gain equations show, for high noise (large R_Hxy) the gain L increases as SIGMA increases. As N_fade is decreased or the diagonal elements of Q are increased, the Kalman again will increase and the system will become more responsive to changes in the observed transfer function Hxy.

Unlike the local estimator, the trend estimator, when implemented using an extended Kalman filter, does not require pre-processing signal averaging; rather, the Kalman filter directly inputs the noisy, "raw" Hxy measurements. If the noise is high, then the Kalman gain is reduced by an increase in the locally measured observation covariance matrix R_Hxy. Furthermore, increasing N_fade when the signal-to-noise ratio (SNR) is low will increase the exponential memory of the trend estimator—the less the noise is, the greater the influence of past values is allowed to be in determining the trend. Thus, as noise increases, the gain is reduced and the exponential integration is increased.

Together, R_Hxy and N_fade create an adaptive Kalman filter that provides an accurate but slowly responding estimation of the trend of CCO for low SNR and a faster estimation of CCO for higher SNR. By changing N_fade one can thus adjust the trade-off between speed and accuracy. The local estimator, however, can be forced to consider only local averaged data, which guarantees acceptable responsiveness at the expense of accuracy.

Note that the trend estimator periodically inputs Hxy, which it processes based on an assumption that the cardiac output is substantially described as an LTIS. A new transfer function measurement is available only once per PRBS run of time data. The dual-estimation method according to the invention is therefore highly undersampled when compared to a traditional time-domain Kalman filter.

Because of the undersampling, if a patient with a high SNR experience a large change in cardiac output between measurements of the transfer function Hxy then it is possible for the trend estimator's model to diverge completely from the observed data. At low SNR, the filter gain is lower, the integration time is greater, and the filter tends to track the data slowly. One advantage of the invention is that divergence of the trend estimator can be detected by comparing its results with those of the local estimator. The Kalman trend estimator, on the other hand, "helps" the local estimator by generating the value R_Hxy($\omega_n$), which the local estimator uses to determine weights in its cost function (Equation 13).

The three-parameter local estimator described above will inherently track high-SNR data. At low SNR, however, it is preferred to use a two-parameter model in which τ is controlled by the Kalman trend estimator since there may still be too much noise in the averaged data for the local estimator to accurately estimate τ. The Hxy_ln(X) model is such that the estimation errors for dc and τ are highly correlated. If τ is underestimated then dc will be overestimated and vice versa. By letting τ be controlled by the trend estimator, which automatically extends its integration time for noisy data, the ability of the local estimator to estimate dc (and thus CCO) is improved.

Experience has indicated that the ability of either or both of the estimators to accurately estimate CCO may be significantly affected by any of several noise sources or characteristics. These include: non-stationary, highly correlated noise commonly associated with temperature noise in the pulmonary artery; respiratory temperature noise; noise caused by a drug bolus; noise caused by surgical procedures; electronic noise caused by bad connections; electromagnetic interference (EMI) from modern surgical instruments; coughing by the patient; and spontaneously (not on a ventilator) and irregularly breathing patients.

The invention therefore provides two different types of noise rejection: 1) signal conditioning; and 2) PRBS run editing. The signal conditioning procedure according to the invention minimizes the effects of low-frequency noise and sample outliers. To remove the low-frequency noise, a run-length moving average filter is preferably used. To remove outliers, the invention includes a noise editor, which detects and removes measurements that statistically cannot be valid temperature signals.

In PRBS run editing, the processor determines that no useful information can be extracted from the current PRSB block of temperature data. It then "intercepts" and discards this data so that it cannot corrupt the local and trend estimates. For example, a poor cable connection typically shows up as a triangular feature in the Cxy data. When this condition is detected, the associated Hxy data is not processed. As an additional feature of run editing according to the invention, if any of the elements of the state vector X suddenly undergoes a large excursion from what would be expected with Gaussian noise, then the processor indicates a "Gaussian edit" condition which prevents the Kalman trend estimator from updating its state vector X.

Low-frequency signal conditioning

Figure 6:
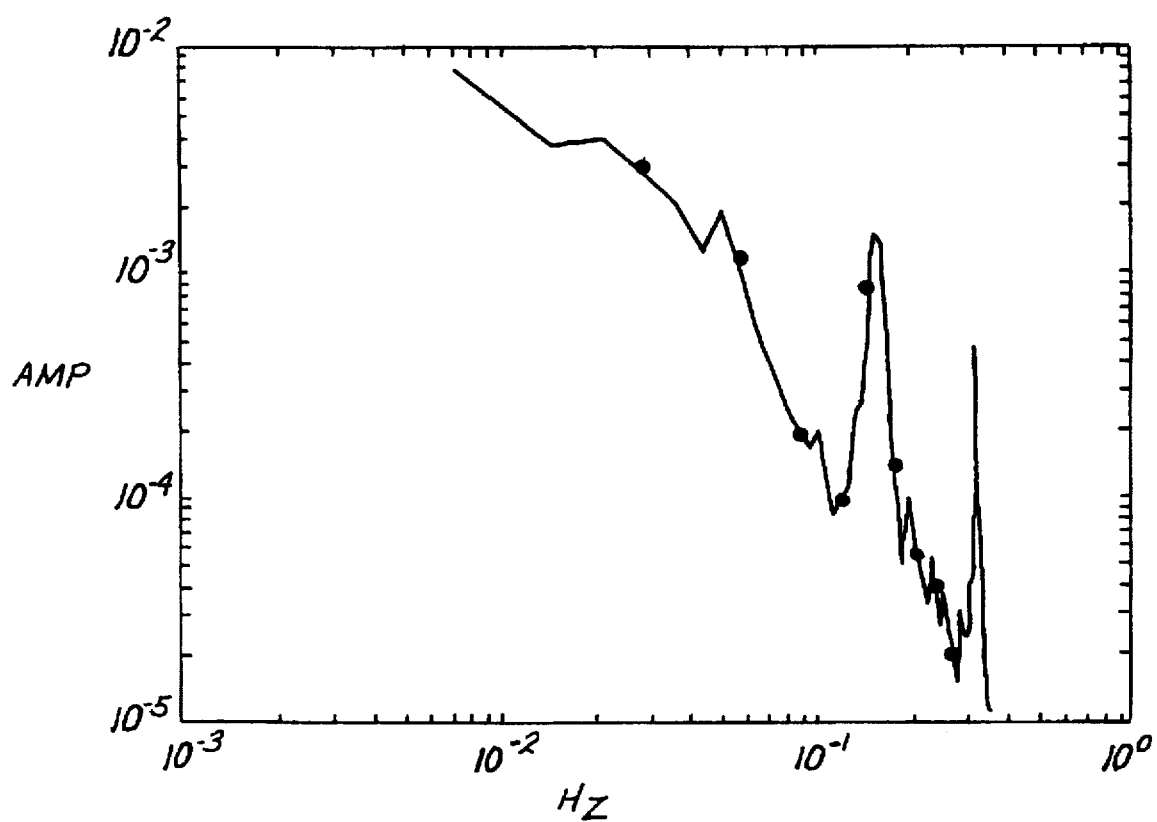
FIG. 6 illustrates a temperature noise spectrum.

FIG. 6 illustrates the temperature noise power spectrum for a typical patient on a ventilator. Two main features of the noise are: 1) the large increase in noise power at the lower frequencies; and 2) the first two harmonics of the ventilator noise at about f=0.15 Hz and f=0.3 Hz.

The powerful noise below about f=0.05 Hz is particularly problematic since the cardiac output estimate is based on an estimate of the zero-frequency gain being divided into a constant. In order to eliminate or at least lessen the interference caused by the harmonics, the invention preferably adjusts the PRBS pulse duration Tc in the manner described in U.S. Pat. No. 5,146,414 (McKown) so that the PRBS harmonics fall to either side of the ventilator's fundamental frequency (and thus its harmonics). Since this procedure is known, it is not described further below.

The low-frequency signal-conditioning method according to the invention takes advantage of the periodicity of the PRBS signal to remove noise trends. Provided that the cardiac output is substantially constant, the PRBS signal component in the temperature data sums to a constant over any time interval that is equal to the length of the PRBS sequence, regardless of when during the PRBS cycle one begins to sum. The invention therefore includes a trend-removal filter, which is preferably a moving average filter whose length is the same as that of the PRBS run. The factors that determine this length are explained above.

Figure 7:
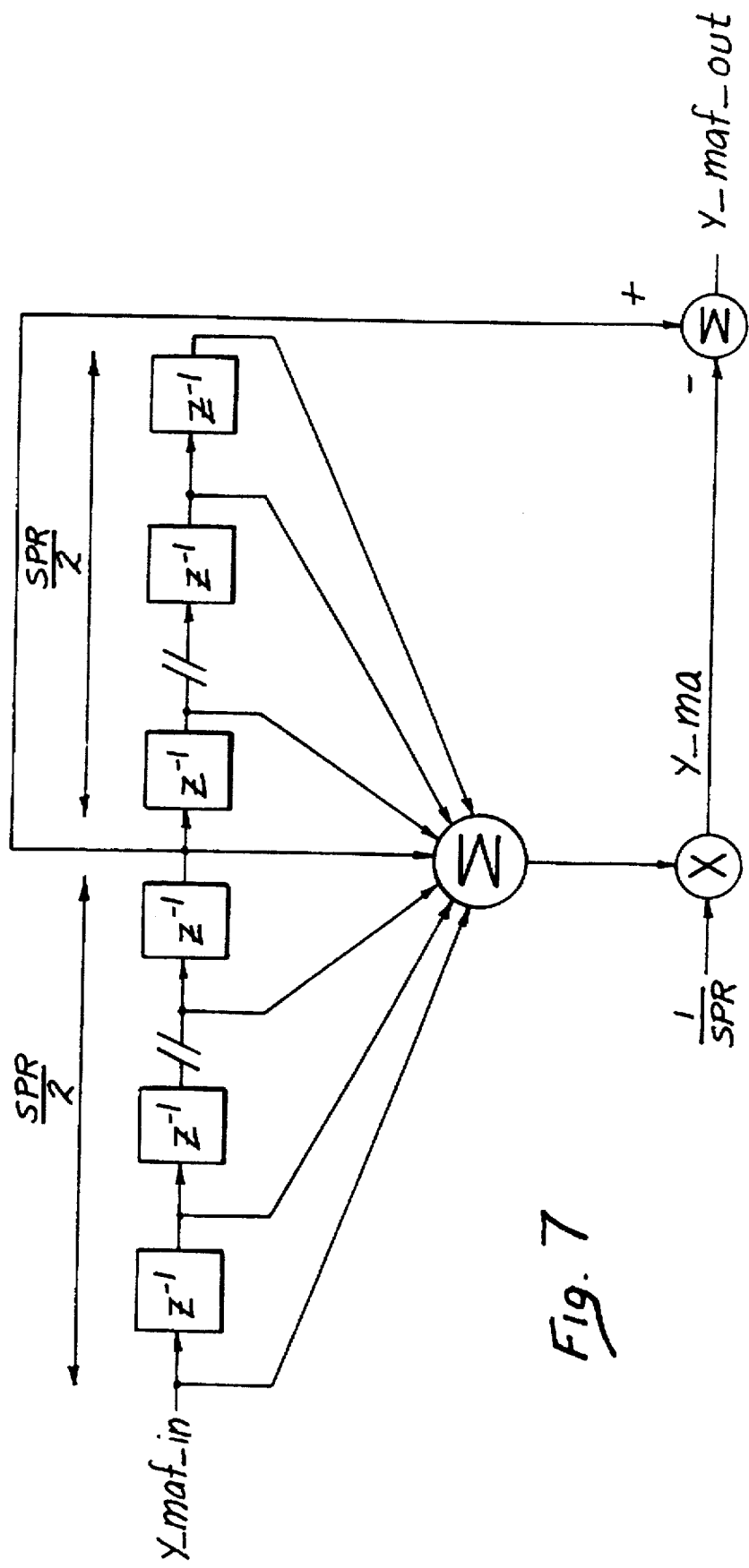
FIG. 7 is a block diagram of a trend-removal filter used in the preferred embodiment of the invention.

FIG. 7 is a block diagram that illustrates the preferred structure of the trend-removing, moving average filter used to remove low-frequency noise from the temperature data from the thermistor. The terms in FIG. 7 are as follows:

SPR=the number of samples per PRBS run;

$z^{-1}$=the conventional backward time-shift operator, so that $z^{-1}[y\_maf\_in(n)]=[y\_maf\_in(n-1)]$, which is simply the most recent previous value of the measured blood temperature;

y_maf_in=y_maf_in(t) is the "raw" temperature data as measured by the thermistor in the pulmonary artery. It represents the input data to the moving average filter.

y_ma=y_ma(t) is a normalized output signal from the moving average filter. Normalization is by multiplication by 1/SNR.

y_maf_out=y_maf_out(t) is the zero-mean temperature data with the noise "drift" removed, that is, the output from the moving average filter shown in FIG. 7.

As the figure shows, the current and (SPR-1) most recent previous values of the temperature signal are arithmetically averaged. (A total of SPR values are averaged). The SPR average is then normalized by division by SPR (multiplication by 1/SPR). This normalized average y_ma is then subtracted from the temperature value obtained SPR/2 samples ago, the result being y_maf_out.

To understand the benefit of the moving average filter, notice that a moving average filter of the type shown in FIG. 7 has a Fourier transform of the form sinc(x)=sin(x)/x, which is centered at zero frequency. The preferred filter is thus the well-known "boxcar" filter, which is described in many standard texts on digital signal processing, such as Oppenheim and Schafer's book *Digital Signal Processing*, Prentice Hall, 1975. Since the width of the filter is SPR samples, the filter has zeros spaced Fs/SPR Hz apart, where Fs is the sample frequency. Note that Fs/SPR Hz is also the frequency of the first harmonic of the PRBS signal, and that the filter thus has zeros at all of the harmonics of the PRBS signal. In other words, the harmonics of the PRBS signal—which are, or at least should be—the only ac signal component in the input temperature signal y_maf_in, will be filtered out. Therefore, no ac component remains in y_ma, and the noise remaining in y_ma will be the input temperature noise filtered by the sinc(x) spectrum of the filter.

Figure 8A:
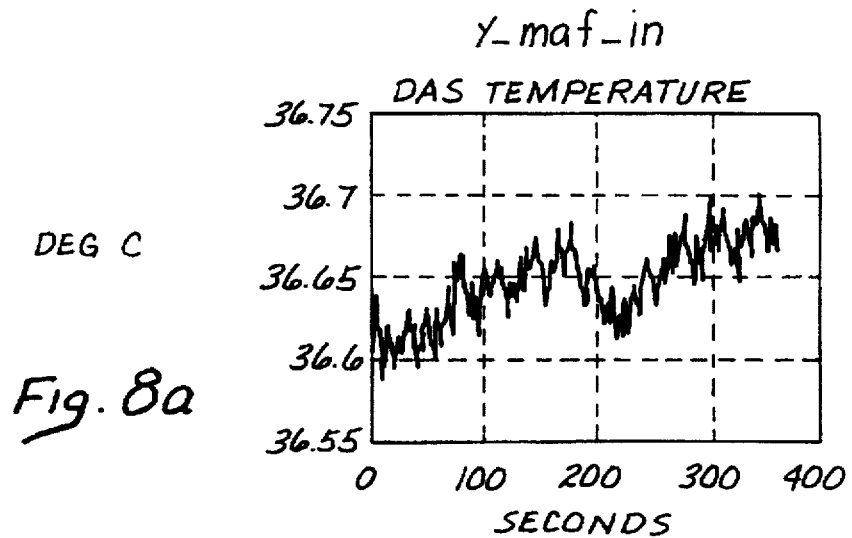
FIG. 8 illustrates temperature data before and after trend removal.
Figure 8B:
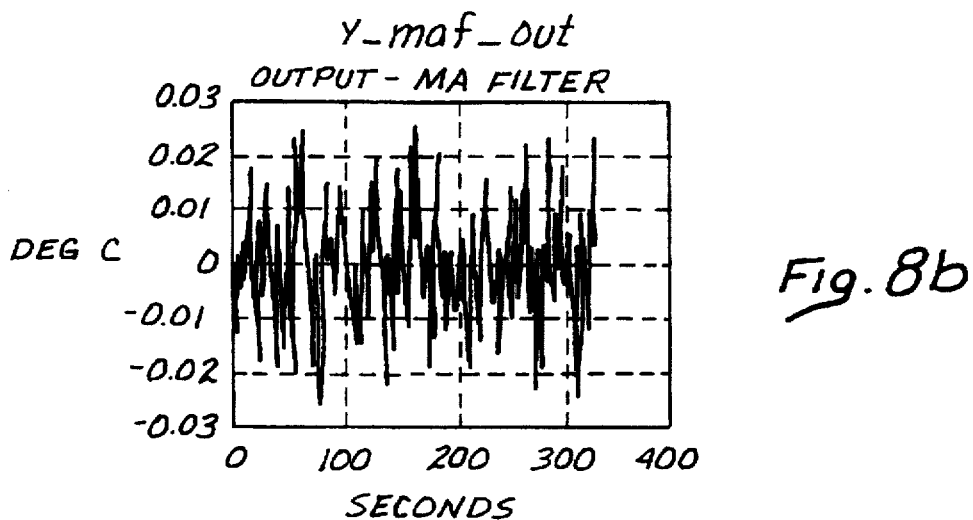

The input signal delayed by SPR/2 samples, that is, $z^{-(SPR/2)}[y\_maf\_in(n)]$ contains three principal superimposed components: the PRBS ac signal (which is used to compute cross-correlations and the transfer function measurements Hxy); the low-frequency input temperature noise; and a dc component common to all the values of y_maf_in. In y_ma, however, the PRBS ac signal is filtered out, leaving only the low-frequency noise and a constant corresponding to the dc component. Subtracting y_ma from y_maf_in(-SPR/2) thus leaves an output signal y_maf_out in which the PRBS ac signal is undistorted: it has zero mean and no drift. FIG. 8(a) is a plot of eleven PRBS runs of raw temperature data, y_maf_in, before filtering using the moving average filter according to the invention, and FIG. 8(b) shows y_maf_out, that is, the result of filtering the raw temperature data. As the figure shows, the general rising trend of y_maf_in is eliminated, so that y_maf_out is "ac-coupled," with zero mean.

It is well known to implement moving-average filters, and any known implementation may be used according the invention. For example, SPR memory positions or a shift register SPR elements long may be used to store the SPR previous values of y_maf_in, which are then summed and shifted (actually, or effectively, by address indexing) each sample period. As one alternative, the known overlap-save fast Fourier transform (FFT) convolution method may also be used.

Although only SPR values of y_maf_in are required by the moving average filter, as is explained below, (nRUNS_y)*SPR values are preferably stored in a memory buffer y_mem for use in signal editing procedures, for example, to reduce the effects of electromagnetic interference. nRUNS_y is a parameter that indicates how many runs of data are to be stored. nRUNS_y should be large enough to allow an approximation of the standard deviation of the temperature values sufficient to identify spurious values.

Tests have shown that nRUNS_y should be at least five, and, for computational efficiency, seven.

EMI Signal Conditioning

Blood-flow monitors such as the invention are often used near powerful sources of electromagnetic interference (EMI) such as certain electro-cauterizing equipment in an operating room. This EMI can contaminate the temperature data and reduce the quality of the CCO estimate.

According to the invention, data corrupted by EMI, or any other powerful, substantially impulsive noise source, is eliminated in two steps. Observe first that although y_mem can be viewed as an (nRUNS_y)xSPR array, or as the concatenation of nRUNS_y vectors, each with elements 1, ..., SPR.

In a first step, the standard deviation $\sigma\_y$ of all the (nRUNS_y)*SPR values in the memory buffer y_mem is calculated in any known manner. A first edit threshold $T_{edit1}=n_{edit1} \cdot \sigma\_y$ is then set, where $n_{edit1}$ is an experimentally or theoretically predetermined parameter. All values in y_mem whose absolute values are greater than $T_{edit1}$ are then set to a predetermined outlier default value, which is preferably zero, since the value is assumed to be so corrupted that it contains insufficient information to determine a "replacement" value. The remaining values form a working vector y_edit, which still can be partitioned into nRUNS_y sets of SPR run values. Furthermore, for every value that is identified as an outlier, the corresponding element in an edited-data identification vector y_keep is set to zero; other elements of y_keep are set to one.

Let a "row" index r be the number of the run, r=1, ..., nRUNS_y, and a "column" index s be the number of the sample in a given run, s=1, ..., SPR. Note that y_mem=y_mem(r,s) and y_edit=y_edit(r,s) and recall that one or more of the elements of y_edit(r,s) may have been forced to zero. For each column, let k(s) be the number of non-zero elements in the s'th column of y_edit, that is, the number of temperature values that were less that $T_{edit1}$ (that is, fell within $T_{edit1}$ of the zero mean of y_mem).

According to the invention, from each element y_mem (r,s) is subtracted the arithmetic average of all the non-zero values in column s. The remaining values form an array y_noise, whose elements are residual values used to determine the relative SNR of each run. The array y_noise is further used to identify and eliminate statistical outliers so that they are not included in the cross-correlation with the PRBS reference signal to form Cxx and Cxy. y_noise is thus calculated as follows:

$$y\_noise(r,s) = y\_mem(r,s) - \frac{1}{k(s)} \cdot \Sigma_s y\_edit(s) \quad \text{for } k(s) \neq 0$$

$$= y\_mem(r,s) - \frac{1}{nRUNS\_y} \cdot \Sigma_s y\_mem(s) \quad \text{for } k(s) = 0$$

After y_noise has been computed, the variance ($\sigma^2$) of each of the nRUNS_y sets of data in y_noise is computed in any known manner. Recall that noise variance is equal to noise power. The noise power values are then normalized by dividing each by the maximum. These normalized noise power values are then converted to decibels to form the signals SNR_run_dB.

A second edit threshold $T_{edit2}$ is then formed as $n_{edit2} \cdot (\sigma\_hi\_SNR)$, where $n_{edit2}$ is an experimentally or theoretically predetermined parameter and $\sigma_{13}$ hi_SNR is the average of the normalized power values that are greater than an experimentally or theoretically predetermined cutoff value. The values from the two most recent PRBS runs stored in y_mem that are greater than the second edit threshold are then set to zero and output as y_edit_σ, which corresponds to y_mem, but with statistical outliers having been edited out. y_edit_σ thus is zero-mean temperature data with any trend and statistical outliers removed. In this context, statistical outliers are values that are likely to have occurred because of disturbances such as EMI.

SNR estimation

Both of the estimators according to the invention use an estimate of the signal-to-noise ratio (SNR) of the temperature data, the local estimator in order to adjust the weights $W(\omega_n)$, and the trend (preferably Kalman) estimator to determine its gain adjustment.

Figure 9:
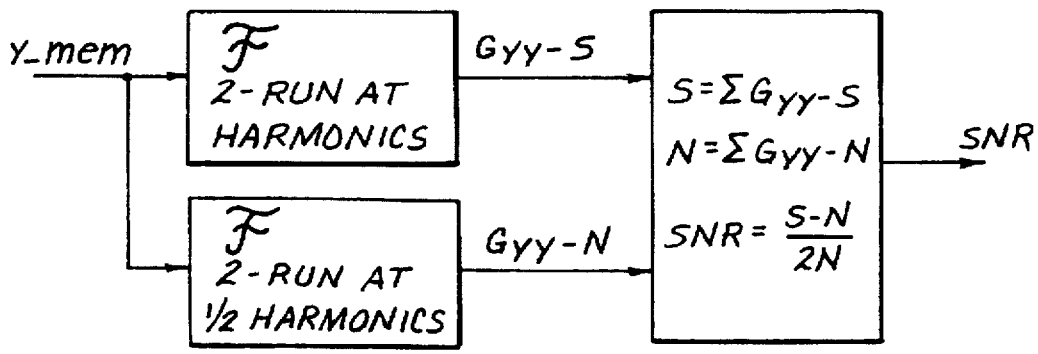
FIG. 9 is a block diagram that shows how SNR is calculated for a trend estimator used in the invention.

As FIG. 9 illustrates, the invention estimates SNR preferably by performing two PRBS cycle-length discrete Fourier transformations (DFT's). The processing system computes a ten-element signal-plus-noise spectrum Gyy_S at each PRBS harmonic, and an 11-element noise-only spectrum Gyy_N at each PRBS half harmonic.

$$G\_yyS(\omega) = \frac{|Ys(\omega)|^2}{SPR \cdot Fs} \text{ and } G\_yyN(\omega') = \frac{|Yn(\omega')|^2}{SPR \cdot Fs}$$

where Ys and Yn are DFT's of the two most recent PRBS runs of temperature data, which are stored in the vector y_mem (see above).

Let y be the 2*SPR length vector of recent temperature data. Then $Ys(\omega) = y \cdot Ws$, where · is the dot product, the elements of $Ws = \exp(-j \cdot m \cdot \omega/Fs) = e^{(-j \cdot m \cdot \omega/Fs)}$ for sample index m=0, ..., 2·(SPR-1) and $\omega = n \cdot 2\pi \cdot Fs/SPR$ for n=1, ..., 10. Similarly, $Yn(\omega') = y \cdot Wn$, the elements of $Wn = \exp(-j \cdot m \cdot \omega'/Fs)$ and $\omega' = (n-\frac{1}{2}) \cdot 2\pi \cdot Fs/SPR$ for n=1, ..., 11.

Because the boxcar window size of the DFT's is 2·SPR, they estimate the spectrum of the temperature data using a filter that has zeros at multiples of the half frequencies of the PRBS harmonics. The advantage of this is that there is no PRBS signal "leakage" between the harmonics of Ys and no PRBS signal power in Yn. The ten elements of Gyy_S therefore represent the signal-plus-noise power in DFT bins centered on the first ten PRBS harmonics and the 11 elements of Gyy_N represent the pure noise power in DFT bins centered on the first 11 PRBS half-harmonics.

Gyy_S and Gyy_N allow the invention to estimate the matched filter bandwidth SNR for the two PRBS runs of temperature data, which are associated with each observed transfer function:

$$SNR = (\Sigma S - \Sigma N)/(2 \cdot \Sigma N)$$

where ΣS and ΣN are the sums of the elements of Gyy_S and Gyy_N, respectively. To avoid sensitivity to ventilator frequencies, the sums are preferably limited to the first three PRBS harmonic elements for Gyy_S and the first four for Gyy_N.

Since this estimate of SNR is derived from the same two PRBS runs of temperature data that provide the latest measurement of the power-temperature transfer function Hxy, it is a good signal strength parameter to use for local estimator weighting and Kalman gain control.

Bolus noise run editing

An attending clinician often uses the injectate port of the pulmonary artery to deliver drugs intravenously. These injections are usually in the form of a 1–10 cm³ fluid bolus at room temperature. It is also common to inject a saline solution to flush the catheter lumens. In either case, the thermistor detects the bolus as a large negative transient (room temperature is much less than normal blood temperature) in the measured blood temperature. It is difficult simply to filter out such bolus induced signals, since they often have a noise component that is 10–30 dB greater than the CCO temperature signal, with substantially the same transfer function shape. If such data is allowed to reach the estimators, the resulting CCO estimates will be erroneously low.

According to the invention, the system's processor examines the measured temperature data in y_mem. If the difference between the maximum and the minimum temperatures values (over all the runs stored in y_mem) exceeds a experimentally predetermined range threshold $T_{range}$, then all the data for the most recent run is either deleted or the run is otherwise flagged as invalid so that it is not used in any further calculations.

Transfer function measurement

As is described above, the invention preferably uses a PRBS correlation technique to measure a frequency-domain power-to-temperature transfer function Hxy. The transfer function Hxy measurements are obtained by cross-correlating an ideal PRBS wave form and Fourier transforming the resulting Cxx and Cxy correlation data.

Figure 10:
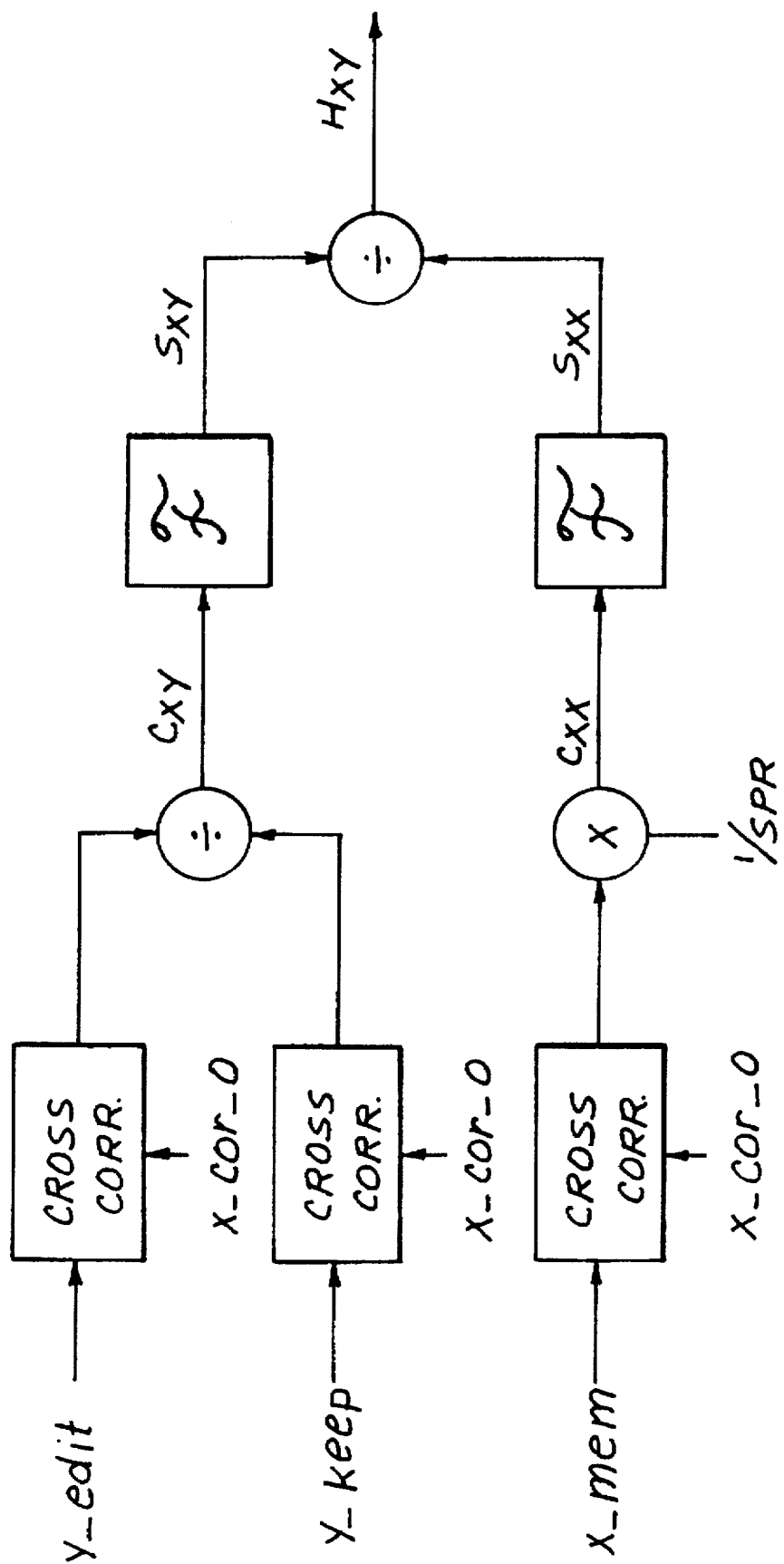
FIG. 10 is a block diagram that illustrates the way in which input power and sensed temperature data is used in the invention to measure a channel transfer function.

See FIG. 10. Let x_mem be the vector of the 2·SPR most recent sensed input power values and let x_cor_0 be a zero-mean SPR-length PRBS signal, which may be generated in any known manner. First, x_cor_0 is correlated with the last two runs of the zero-mean, outlier-edited temperature data y_edit, that is, the PRBS signals; the result is an unnormalized cross-correlation value Cxy_un.

In order to properly normalize the PRBS correlation data, x_cor_0 is then correlated with the vector y_keep, which, as is described above, contains "ones" only in elements corresponding to values of temperature data not found to be outliers. The result of this correlation is an SPR-length vector N_prod, which contains the number of lag-products that contribute to each lag of the correlation vector Cxy. Element-by-element division of Cxy_un produces a normalized temperature cross-correlation vector Cxy for lags 0 to (SPR-1). Note that if there are no outlier edits (all elements of y_keep are equal to one), then all elements of N_prod are equal to SPR.

Similarly, x_cor_0 is correlated with the non-edited power data x_mem, and is normalized by division by SPR. The result is the PRBS cross-correlation vector Cxx for lags 0 to (SPR-1).

The values Cxy and Cxx are then converted to the frequency domain using Fourier transformation at the PRBS harmonics. The respective results are Sxy and Sxx, which, when divided element-by-element, provide the power-to-temperature measured transfer function Hxy.

Transfer function noise estimation

As is described above, the preferred trend estimator (a Kalman filter) uses R_Hxy, a 10×10 complex matrix containing the noise covariance in the ten-element complex vector Hxy. The more thermal noise there is in the pulmonary artery, the larger the elements of R_Hxy will be. Although it is possible to calculate all 100 elements of R_Hxy, the inventors have discovered that better performance is obtained by calculating only the diagonal elements of R_Hxy (the auto-correlation elements). Not only does this simplification provide consistency with the assumption of white noise in a Kalman filter, but it also reduces computational complexity.

The covariance matrix R_Hxy may be computed using the well-known formula for statistical variance. Thus, a predetermined number nHxy of measured transfer function values Hxy are stored in a memory buffer Hxy_mem. The number nHxy may be chosen by experiment; in one prototype of the invention, 15 values of nHxy were accumulated in Hxy_mem. The k'th of the ten diagonal elements of R_Hxy is then computed as follows:

$$Hxy\_mean(k) = \frac{1}{nHxy} \cdot \sum_{n=1}^{nHxy} Hxy\_mem(k,n)$$

$$R\_Hxy(k) = \frac{1}{nHxy-1} \cdot \sum_{n=1}^{nHxy} |Hxy\_mem(k,n) - Hxy\_mean(k)|^2$$

for PRBS harmonics $k = 1, \ldots, 10$

The values of R_Hxy may then further be smoothed using known methods.

Responsiveness control

It is pointed out above that the responsiveness of the Kalman trend estimator can be adjusted both by the fading memory scalar f and the random walk covariance matrix Q. In particular, the covariance matrix SIGMA(n) is a function of SIGMA(n−1) (see above), which is extrapolated according to the relationship SIGMA(extrapolated)=f*SIGMA+Q.

In the preferred embodiment of the invention, f fades exponentially, that is, $f=e^{(-N\_fade)}$, where N_fade is chosen to be the greater of the block size of the local estimator (the number of PRBS runs it includes for calculating each estimate) or the average (possibly smoothed) SNR of the block. The fading memory constant therefore gets bigger, and the influence of previous SIGMA values decays faster the larger or noisier a block is.

The random walk covariance matrix Q is 3×3 a diagonal matrix whose i'th element $Q(i,i)=(X\_frac*X(i))^2$ where X_frac determines the standard deviation of the random walk in terms of a fraction of the i'th state vector element X(i). Until the trend estimator has received enough sequential run data to generate recursive estimations, X_frac is preferably set proportional to a sigmoid function of the average SNR, for example, X_frac $\alpha$ $(1+1/SNR\_dB)^{-1}$, where SNR_dB is the average SNR expressed in decibels.

After enough values of Hxy have been measured (usually, three) for the trend estimator to begin iteration, then X_frac is preferably set to an experimentally determined small constant (to prevent too much excursion in the steady state); in one test of the invention, X_frac was set to 0.02.

Non-Gaussian noise run editing

It is known that Kalman filters are optimal least-squares estimators if the observation noise has a Gaussian amplitude distribution and is uncorrelated between observations, that is, it is so-called white Gaussian noise (WGN). It is also known that if the observation noise if WGN then the error in the Kalman filter's state vector estimate is also WGN.

The temperature in the pulmonary artery if often correlated from one PRBS run to the next and its amplitude distribution is often non-Gaussian. The sequence of observed transfer functions Hxy (which are linearly related to the temperature signal y(t)) are therefore also correlated and non-Gaussian. These characteristics violate the statistical assumptions that underlie Kalman filters and can lead to significant estimation noise or bias.

According to the invention, the system examines statistics of the elements of the state vector X and parameter covariance matrix and determines if they satisfy Gaussian amplitude distributions. If they do, then the Kalman filter trend estimator proceeds normally. If not, then the trend estimator does not update the state vector and the covariance matrix until the next estimation cycle and the corresponding observed transfer function is simply ignored and the CCO estimate is not updated.

Of the three parameters in the state vector X=[dc, µ, τ], the statistics that the invention examines for µ, τ are the parameters themselves. For the dc parameter, however, the system evaluates its inverse, since the quantity of interest—CCO—is inversely related to dc.

According to the invention, nMEM_X previous values of a statistics vector X_stat=[1/dc, µ, τ] are stored in memory. In one prototype of the invention, nMEM_X was set to fifteen, which provided meaningful statistics without adding needless delay; any other number as long as it is large enough to provide meaningful statistics.

A mean vector X_mean is then computed as the arithmetic mean of the nMEM_X vectors. The standard deviation of the nMEM_X values of 1/dc, µ, and τ are then individually either computed, using standard formulas, or are estimated, to form a standard deviation vector X_σ. In a prototype of the invention, computation time was reduced by setting X_σ=std_frac·X_mean, where std_frac was a vector of predetermined constants that were determined experimentally to be [0.12, 0.16, 0.16]. X_σ is then preferably multiplied by a predetermined but adjustable deviation constant k_σ, which determines by how much a statistic may deviate before it is edited out.

For each new estimated X, the system then computes the absolute value of the difference between the current statistic values [1/dc, µ, τ] and k_σ·std_frac·X_mean. If any element of the resulting comparison is greater than an experimentally or theoretically determined Gaussian edit threshold value $T_{G\_edit}$, then the current estimate is edited out and the state vector is not updated. For example, if k_σ=2, then the Kalman filter will not update the state vector if any of its statistical parameters are outliers, that is, more than "two-sigma" away from the mean. If, for example, k_σ=2, then parameters values more than "two-sigma" away from the mean are identified as outliers.

Trend divergence detection

As is mentioned above, if a patient with a high SNR undergoes a large change in cardiac output between consecutive transfer function measurements then the undersampled Kalman filter used as the preferred trend estimator may diverge. The local estimator, however, is stable even for high SNR. According to the invention, the estimates from the two estimators are compared to determine whether the Kalman filter's estimates indicate likely divergence.

After each Kalman update, the system computes a relative trend error vector Cxy_trend_error as the scalar error in percent of the ratio of: 1) the root-mean-square (RMS) difference between the averaged cross-correlation vector Cxy_avg and the modelled Cxy_model (both defined above); to 2) the RMS of the signal Cxy_avg itself. A relative local error vector Cxy_local_error is similarly calculated using, for calculation of Cxy_model, the value of the parameter vector X determined from the most recent local estimation.

Let Hxy_model be the transfer function values obtained using the current parameters of X in the lagged-normal model. The system also computes a relative trend error vector Hxy_error_trend as the ratio between: 1) the square root of the sum of the weighted differences between the average measured transfer function values Hxy_avg and the modelled transfer function values Hxy_avg; and 2) the magnitude of Hxy_avg itself. A relative local error vector Hxy_local_error is similarly calculated using, for calculation of Hxy_model, the value of the parameter vector X determined from the most recent local estimation.

The ratios (Cxy_trend_error)/(Cxy_local_error) and (Hxy_trend_error)/(Hxy_local_error) are then computed and if either exceeds a predetermined divergence threshold $T_{div}$, then the system assumes that the trend estimate is unreliable, rejects the current trend estimate. It also resets the trend estimator so that its parameter and other vectors, such as X, as set equal to the corresponding values from the local estimator, as when the system first is started up. $T_{div}$ may be any experimentally or theoretically predetermined function or a constant, and is preferably a function of the measured SNR.

Trend convergence detection

It is helpful for the user to know not only when the Kalman filter has diverged, but also when the displayed CCO trend values represent reliable, steady-state CCO values. For example, when the system is started up, it may take several PRBS runs before an adequately accurate CCO value is available. According to the invention, until that time, the Kalman state vector X is set equal to the state vector X from the local estimator. Any or all of several alternative convergence tests may be used.

As one example, after the system computes a current CCO estimate CCO(n) using the current dc estimate in Equation 8, the current value may be compared with the most recent previous value CCO(n−1). If the change (preferably expressed in percent relative to the average) is smaller than an experimentally or theoretically predetermined threshold $T_{\delta CCO}$ then the system may assume convergence, that is, the estimate is assumed to represent a steady-state estimate if:

$$100 \cdot \frac{|CCO(n) - CCO(n-1)|}{1/2 \cdot [CCO(n) + CCO(n-1)]} < T_{\delta CCO}$$

As another example, after an experimentally predetermined number of valid CCO trend estimates have been computed (to give the trend estimator time to reach a steady-state estimate), the errors Cxy_trend_error and Hxy_trend_error will decrease. The system therefore indicates convergence whenever either (or both) of these values is less than an error convergence value $T_{eCCO}$, which may be determined by experiment.

Non-PRBS input power signals

The preferred input heat signal according to the invention is generated as a pseudo-random binary sequence (PRBS) since it allows for efficient correlation and since its power is discretely spread in harmonics that cover the spectral region of interest. Other input signal patterns may, however, also be used according to the invention. For example, if the applied input heat signal is in the form of a given number of sinusoidal components (see, for example, Newbower), then the various filters and transformation (such as FFT) circuits will be tuned to the known input frequencies, which will not need to be computed. Banks of analog filters could even be used instead of Fourier transformations in order to provide rough measurements of the transfer function Hxy of the channel.

As yet another example, the output of the dispersive filter used in the spread-spectrum system of Dixon, et al. is the impulse response of the channel. Fourier transformation of this impulse response also yields a transfer function measurement. The correlation steps of the invention may then be eliminated as long as the remaining equations are suitably adjusted; such changes may be determined theoretically.

Non-thermal indicators

Moreover, in the invention, heat is used as the indicator that is injected into the bloodstream at an upstream position and temperature is the downstream signal that is sensed to form the basis of the CCO estimates. This is advantageous because heat indicator does not accumulate in the patient and is relatively safe, well-understood, easy to control and sense. Other conventional indicators may, however, also be used according to the invention. In such cases, the transfer function of the channel can still be modelled, preferably using the lagged normal model, to provide a state vector with a gain parameter. The techniques described above can then be applied with at most slight modification to provide the local and trend estimates of cardiac output with the same advantages described above. Needed modifications will be readily determined by known experimentation and theoretical calculations.

I claim:

1. A method for estimating blood output through a flow region of a patient's body, comprising the following steps:
   A) injecting an indicator as an indicator input signal having an input signal profile and a period into an upstream position in the flow region;
   B) sensing the presence of the indicator at a downstream position in the flow region to determine an indicator output signal;
   C) estimating as a predetermined function of the input signal profile and the indicator output signal both a local blood output value over a local estimation time, and a trend blood output value over a trend estimation time, in which the trend estimation time is longer than the local estimation time, thereby providing estimated blood output values corresponding to both relatively fast and slow changes in blood output.

2. A method as in claim 1, in which the step of estimating the trend output value comprises the step of recursively estimating the trend output value.

3. A method as in claim 2, in which the step of recursively estimating comprises Kalman filtering.

4. A method as in claim 2, in which the step of estimating the predetermined function in turn comprises the following steps:
   measuring values of a frequency-domain transfer function between the indicator input signal and the indicator output signal for each period of the indicator input signal, the measured frequency-domain transfer function forming input signals for both local blood output value and trend blood output value estimation;
   selecting state parameters of a predetermined transfer function model relating the indicator output signal to the indicator input signal;
   determining optimal local state parameters as a predetermined optimization function of the transfer function model and the measured frequency-domain transfer function values, and estimating the local blood output value as a predetermined output function of at least one of the optimal local state parameters; and
   recursively estimating optimal trend state parameters by Kalman filtering the measured frequency-domain transfer function values, and estimating the trend blood output value as the predetermined output function of at least one of the optimal local state parameters.

5. A method as in claim 4, further including the step of initializing the Kalman filtering step using the optimal local state parameters.

6. A method as in claim 4, further including the following steps:
   A) generating the input signal profile as a pseudo-random binary sequence (PRBS);
   B) determining an autocorrelation value Cxx of the input signal and converting the autocorrelation value Cxx to the frequency domain;
   C) determining a cross-correlation value Cxy between the input signal and the output signal and converting the cross-correlation value Cxy to the frequency domain; and D) computing the measured frequency-domain transfer function values as a predetermined function of the quotient between the frequency-converted cross-correlation and autocorrelation values.

7. A method as in claim 4, further including the step of removing any low-frequency noise trend from the indicator output signals before estimating either the local blood output value or the trend blood output value.

8. A method as in claim 1, in which the step of estimating the predetermined function comprises measuring a frequency-domain transfer function between the indicator input signal and the indicator output signal for each period of the indicator input signal, the measured frequency-domain transfer function forming input signals for both local blood output value and trend blood output value estimation.

9. A method as in claim 1, further including the following steps:

grouping sensed indicator output signals into a sequence of runs, each run comprising the indicator output signals sensed during a predetermined run period;

determining a signal edit threshold and a signal edit condition as predetermined functions of the indicator output signals;

comparing the indicator output signals with the signal edit threshold; and setting to a predetermined default value any indicator output signals that meet the signal edit condition before the step of estimating the blood output values.

10. A method as in claim 9, wherein the step of determining the signal edit condition comprises comparing absolute values of the indicator output signals with the signal edit threshold, the signal edit condition being that the absolute values of the indicator output signals exceed the signal edit threshold, thus indicating the presence of a substantially impulsive noise source in the flow region.

11. A method as in claim 9, wherein the step of determining the signal edit condition comprises determining a maximum output value range for each run, and the step of setting to the predetermined default value comprises setting to the predetermined default value all output signals in any run whose maximum output value range exceeds the signal edit threshold, thus indicating the presence of a non-impulsive noise source in the flow region.

12. A method for estimating blood output through a flow region of a patient's body, comprising the following steps:

A) injecting a thermal indicator as an indicator input signal having a pseudo-random binary sequence (PRBS) input signal profile and a period into an upstream position in the flow region;

B) sensing the presence of the indicator at a downstream position in the flow region to determine an indicator output signal;

C) removing any low-frequency noise trend from the indicator output signals;

D) selecting state parameters of a predetermined transfer function model relating the indicator output signal to the indicator input signal;

E) determining an autocorrelation value Cxx of the input signal and converting the autocorrelation value Cxx to the frequency domain;

F) determining a cross-correlation value Cxy between the indicator input signal and the indicator output signal and converting the cross-correlation value Cxy to the frequency domain;

G) computing measured transfer function values as a predetermined function of the quotient between the frequency-converted cross-correlation and autocorrelation values;

H) determining optimal local state parameters as a predetermined optimization function of the transfer function model and the measured transfer function values, and estimating a local blood output value as a predetermined output function of at least one of the optimal local state parameters; and I) recursively estimating optimal trend state parameters by Kalman filtering the measured transfer function values, and estimating a trend blood output value as the predetermined output function of at least one of the optimal local state parameters.

13. A system for estimating blood output through a flow region of a patient's body, comprising:

A) injection means for injecting an indicator as an indicator input signal having an input signal profile and a period into an upstream position in the flow region;

B) indicator sensing means for sensing the presence of the indicator at a downstream position in the flow region to determine an indicator output signal;

C) estimation means including a local estimator for estimating over a local estimation time a local blood output value as a predetermined function of the input signal profile and the indicator output signal, and a trend estimator for estimating a trend blood output value over a trend estimation time, in which the trend estimation time is longer than the local estimation time, thereby providing estimated blood output values corresponding to both relatively fast and slow changes in blood output.

14. A system as in claim 13, in which the estimation means includes a recursive estimator for estimating the trend output value.

15. A system as in claim 14, in which the recursive estimator is a Kalman filter.

16. A system as in claim 14, in which:

transfer function measuring means is provided for measuring values of a frequency-domain transfer function between the indicator input signal and the indicator output signal for each period of the indicator input signal, the measured frequency-domain transfer function forming input signals for both the local estimator and the trend estimator;

the local estimator is provided for determining optimal local state parameters as a predetermined optimization function of the transfer function model and the measured transfer function values, and estimating the local blood output value as a predetermined output function of at least one of the optimal local state parameters; and the trend estimator is a Kalman filter recursively estimating optimal trend state parameters by Kalman filtering the measured transfer function values, and estimating the trend blood output value as the predetermined output function of at least one of the optimal local state parameters.

17. A system as in claim 16, in which the local estimator is connected to the trend estimator, the optimal local state parameters forming initialization state parameters for the Kalman filter.

18. A system as in claim 16, in which:

A) the input signal profile is a pseudo-random binary sequence (PRBS);

B) the transfer function measuring means is further provided:

1) for determining an autocorrelation value Cxx of the input signal and converting the autocorrelation value Cxx to the frequency domain;

2) for determining a cross-correlation value Cxy between the input signal and the output signal and converting the cross-correlation value Cxy to the frequency domain; and 3) for computing the measured transfer function values as a predetermined function of the quotient between the frequency-converted cross-correlation and autocorrelation values.

19. A system as in claim 13, further including transfer function measuring means for measuring a frequency-domain transfer function between the indicator input signal and the indicator output signal for each period of the indicator input signal, the measured frequency-domain transfer function forming input signals for both the local estimator and the trend estimator.

20. A system as in claim 13, further including pre-filtering means for removing any low-frequency noise trend from the indicator output signals before local or trend estimation.

21. A system as in claim 13, further including:

means for grouping sensed indicator output signals into a sequence of runs, each run comprising the indicator output signals sensed during a predetermined run period;

means for determining a signal edit threshold and a signal edit condition as predetermined functions of the indicator output signals;

means for comparing the indicator output signals with the signal edit threshold; and means for setting to a predetermined default value any indicator output signals that meet the signal edit condition before the step of estimating the blood output values.

22. A system as in claim 21, wherein the means for determining the signal edit condition comprises means for comparing absolute values of the indicator output signals with the signal edit threshold, the signal edit condition being that the absolute values of the indicator output signals exceed the signal edit threshold, thus indicating the presence of a substantially impulsive noise source in the flow region.

23. A system as in claim 21, wherein the means for determining the signal edit condition comprises means for determining a maximum output value range for each run, and the means for setting to the predetermined default value sets to the predetermined default value all output signals in any run whose maximum output value range exceeds the signal edit threshold, thus indicating the presence of a non-impulsive noise source in the flow region.

24. A system for estimating blood output through a flow region of a patient's body, comprising:

A) indicator injection means for injecting a thermal indicator having a pseudo-random binary sequence (PRBS) input signal profile into an upstream position in the flow region as an indicator input signal;

B) thermistor means for sensing the presence of the indicator at a downstream position in the flow region to determine an indicator output signal;

C) pre-filter means for removing any low-frequency noise trend from the indicator output signals;

D) transfer function measuring means:

1) for computing an autocorrelation value Cxx of the input signal and converting the autocorrelation value Cxx to the frequency domain;

2) for computing a cross-correlation value Cxy between the indicator input signal and the indicator output signal and converting the cross-correlation value Cxy to the frequency domain;

3) for computing measured transfer function values as a predetermined function of the quotient between the frequency-converted cross-correlation and autocorrelation values;

E) local estimation means for determining optimal local state parameters as a predetermined optimization function of the transfer function model and the measured transfer function values, and estimating a local blood output value as a predetermined output function of at least one of the optimal local state parameters; and F) trend estimation means for recursively estimating optimal trend state parameters by Kalman filtering the measured transfer function values, and estimating a trend blood output value as the predetermined output function of at least one of the optimal local state parameters.

\* \* \* \* \*